(12) United States Patent
Fujii et al.

(10) Patent No.: US 11,796,550 B2
(45) Date of Patent: *Oct. 24, 2023

(54) SAMPLE ANALYZER, SAMPLE ANALYZING METHOD, AND REAGENT CONTAINER HOLDER

(71) Applicant: SYSMEX CORPORATION, Kobe (JP)

(72) Inventors: Takuya Fujii, Kobe (JP); Hironori Katsumi, Kobe (JP); Akio Toyoda, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 170 days.

This patent is subject to a terminal disclaimer.

(21) Appl. No.: 16/785,688

(22) Filed: Feb. 10, 2020

(65) Prior Publication Data

US 2020/0174031 A1 Jun. 4, 2020

Related U.S. Application Data

(63) Continuation of application No. 15/379,549, filed on Dec. 15, 2016, now Pat. No. 10,591,500.

(30) Foreign Application Priority Data

Dec. 17, 2015 (JP) ................................. 2015-246614

(51) Int. Cl.
*G01N 35/02* (2006.01)
*G01N 35/10* (2006.01)
(Continued)

(52) U.S. Cl.
CPC .............. *G01N 35/025* (2013.01); *B01L 9/06* (2013.01); *G01N 21/59* (2013.01);
(Continued)

(58) Field of Classification Search
None
See application file for complete search history.

(56) References Cited

U.S. PATENT DOCUMENTS 5,320,809 A 6/1994 Dunn et al.
5,788,928 A 8/1998 Carey et al.
(Continued)

FOREIGN PATENT DOCUMENTS

CN 101726610 A 6/2010
CN 101806806 A 8/2010
(Continued)

OTHER PUBLICATIONS

Office Action dated Feb. 7, 2021 in a counterpart Chinese patent application.
(Continued)

*Primary Examiner* — P. Kathryn Wright
(74) *Attorney, Agent, or Firm* — METROLEX IP LAW GROUP, PLLC

(57) ABSTRACT

A sample analyzer includes: a reagent container holder including a reagent container holder body configured to hold a reagent container, and a tilt changing part configured to change a tilt of the reagent container holder body; a reagent dispenser configured to aspirate a reagent contained in the reagent container held in the reagent container holder body; a detector configured to detect a signal for analysis from a measurement specimen containing a sample and the reagent dispensed by the reagent dispenser; and a controller that analyzes the sample on the basis of the signal detected by the detector.

18 Claims, 23 Drawing Sheets

(51) Int. Cl.
    *B01L 9/06*     (2006.01)
    *G01N 35/04*     (2006.01)
    *G01N 21/59*     (2006.01)
    *G01N 33/49*     (2006.01)
    *G01N 33/86*     (2006.01)
    *G01N 35/00*     (2006.01)

(52) U.S. Cl.
    CPC ......... *G01N 33/4905* (2013.01); *G01N 33/86* (2013.01); *G01N 35/00732* (2013.01); *G01N 35/04* (2013.01); *G01N 35/1002* (2013.01); *G01N 35/1009* (2013.01); *G01N 2035/00752* (2013.01); *G01N 2035/0406* (2013.01); *G01N 2035/046* (2013.01); *G01N 2035/0443* (2013.01); *G01N 2201/08* (2013.01)

(56) References Cited

U.S. PATENT DOCUMENTS

| | | | |
|---|---|---|---|
| 2007/0229830 A1 | 10/2007 | Yamamoto et al. | |
| 2008/0014118 A1* | 1/2008 | Kitagawa | G01N 35/00663 422/64 |
| 2010/0126286 A1 | 5/2010 | Self et al. | |
| 2012/0321513 A1 | 12/2012 | Nagai et al. | |

FOREIGN PATENT DOCUMENTS

| | | |
|---|---|---|
| CN | 103630696 A | 3/2014 |
| CN | 104950117 A | 9/2015 |
| CN | 104950122 A | 9/2015 |
| EP | 2034320 A2 | 3/2009 |
| JP | H11-295317 A | 10/1999 |
| JP | 2002-055110 A | 2/2002 |
| JP | 3445791 A | 9/2003 |
| JP | 2010-096515 A | 4/2010 |
| WO | 2008/133019 A1 | 11/2008 |
| WO | 2011/105247 A1 | 9/2011 |

OTHER PUBLICATIONS

Office Action dated May 8, 2020 in a counterpart Chinese patent application.
Office Action dated Apr. 7, 2020 in a counterpart Japanese patent application.
Communication pursuant to Article 94(3) EPC dated May 31, 2021 in a counterpart European patent application.
Extended European search report dated Mar. 13, 2023 in a counterpart European patent application.
Chinese Office Action dated Aug. 24, 2022 in a counterpart Chinese patent application.

* cited by examiner

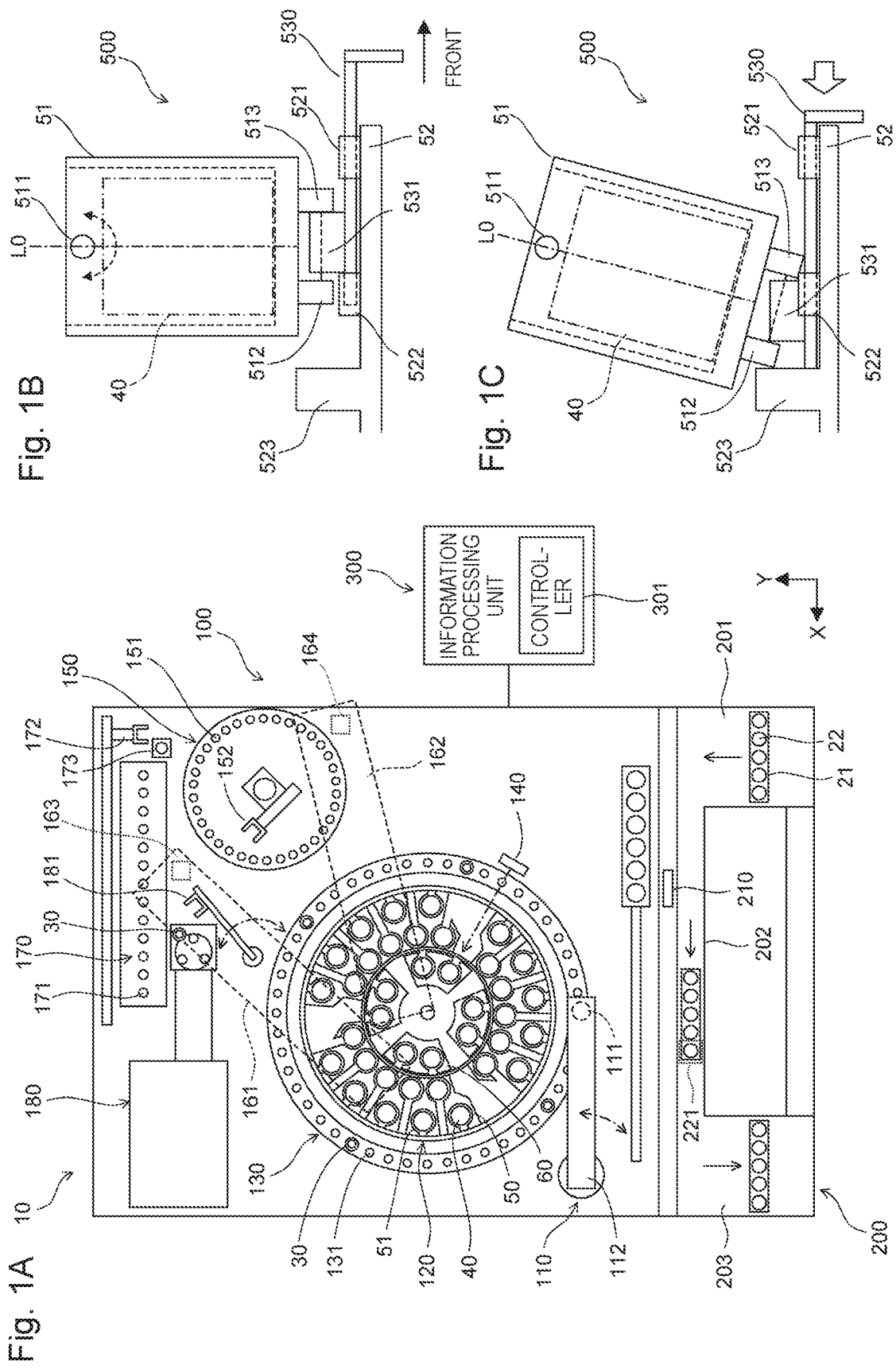

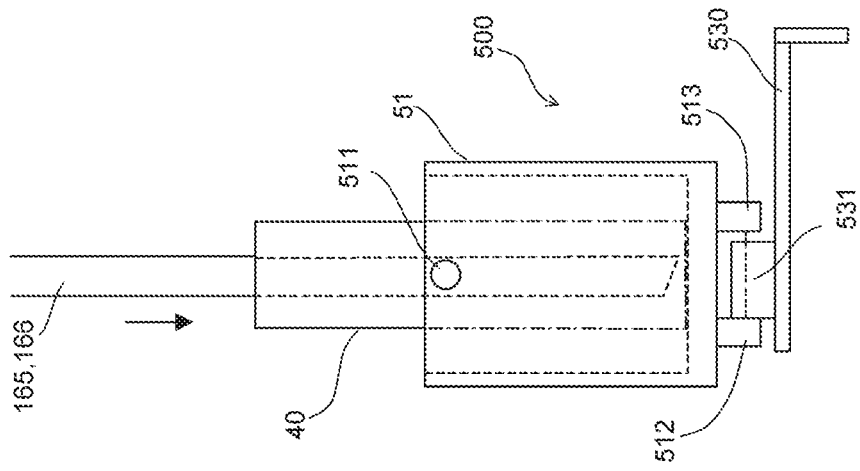
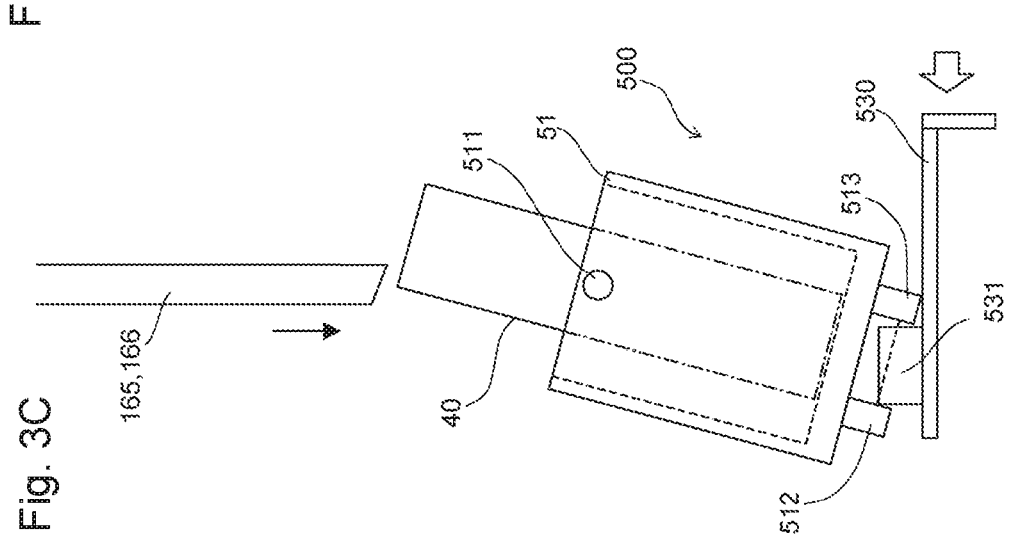
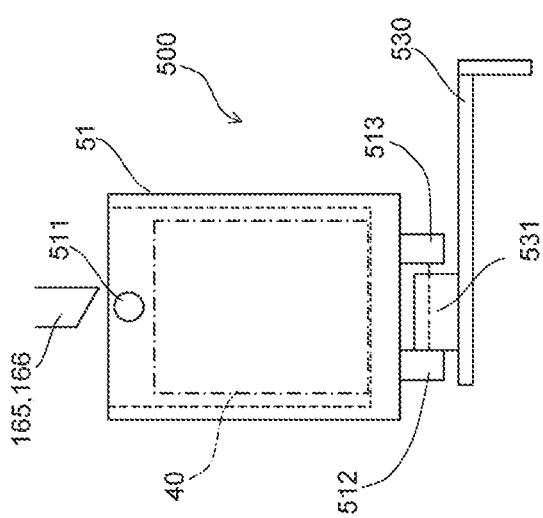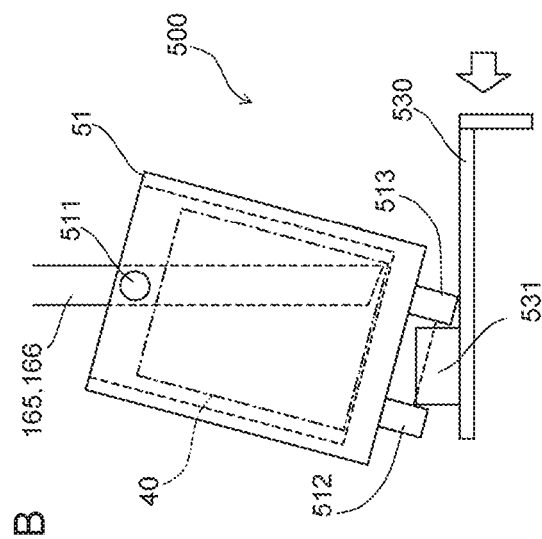

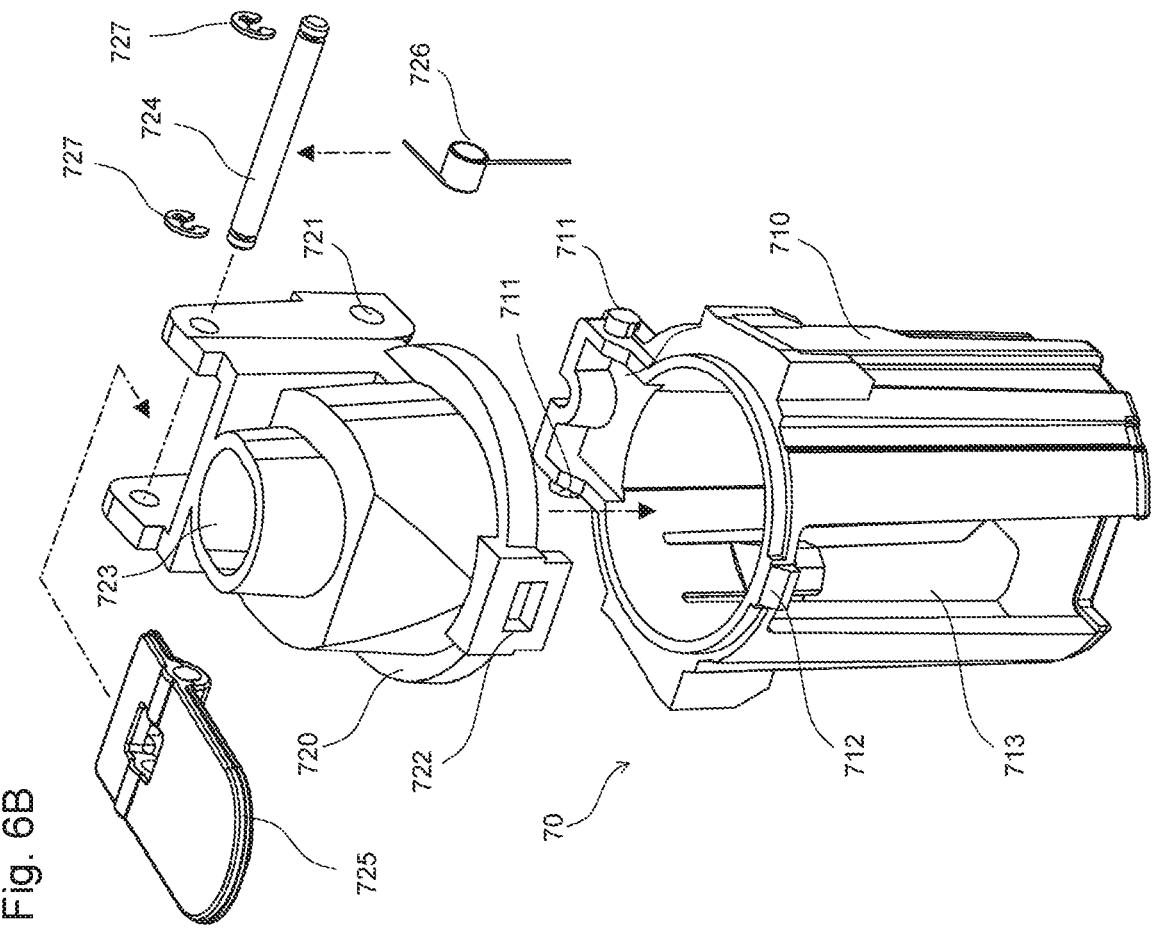
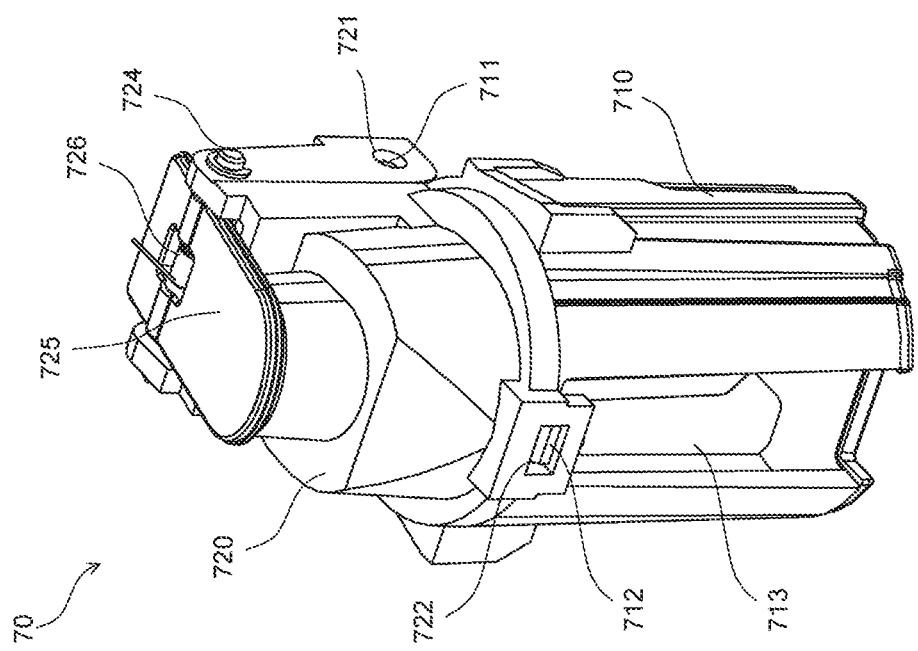

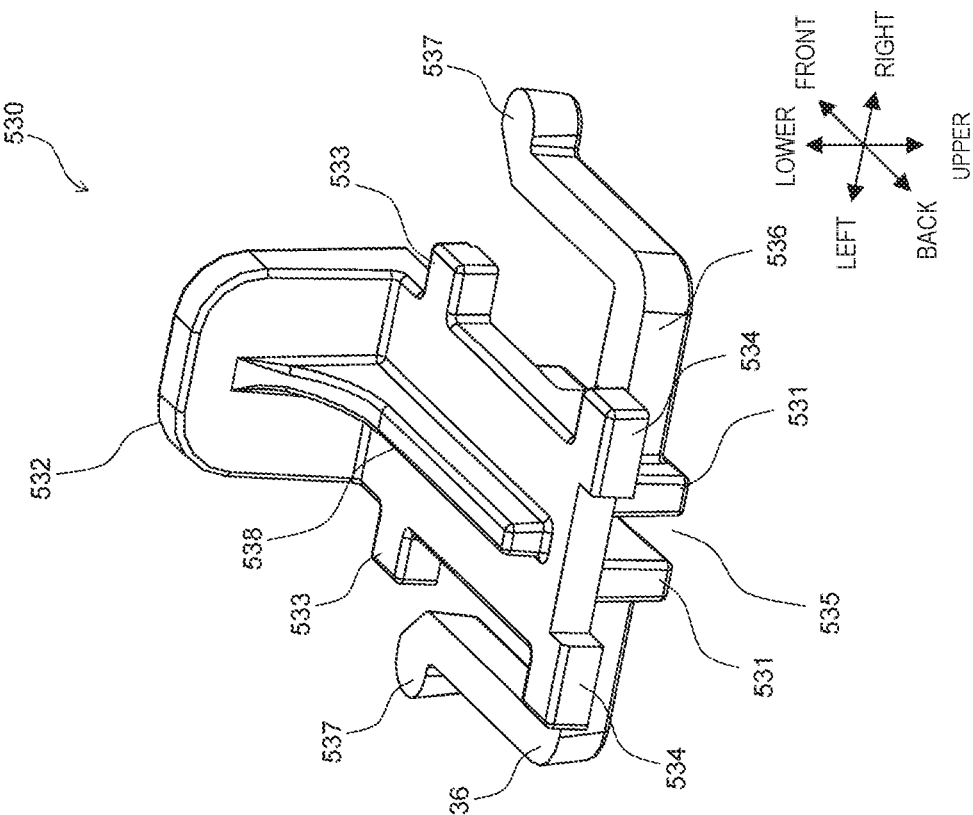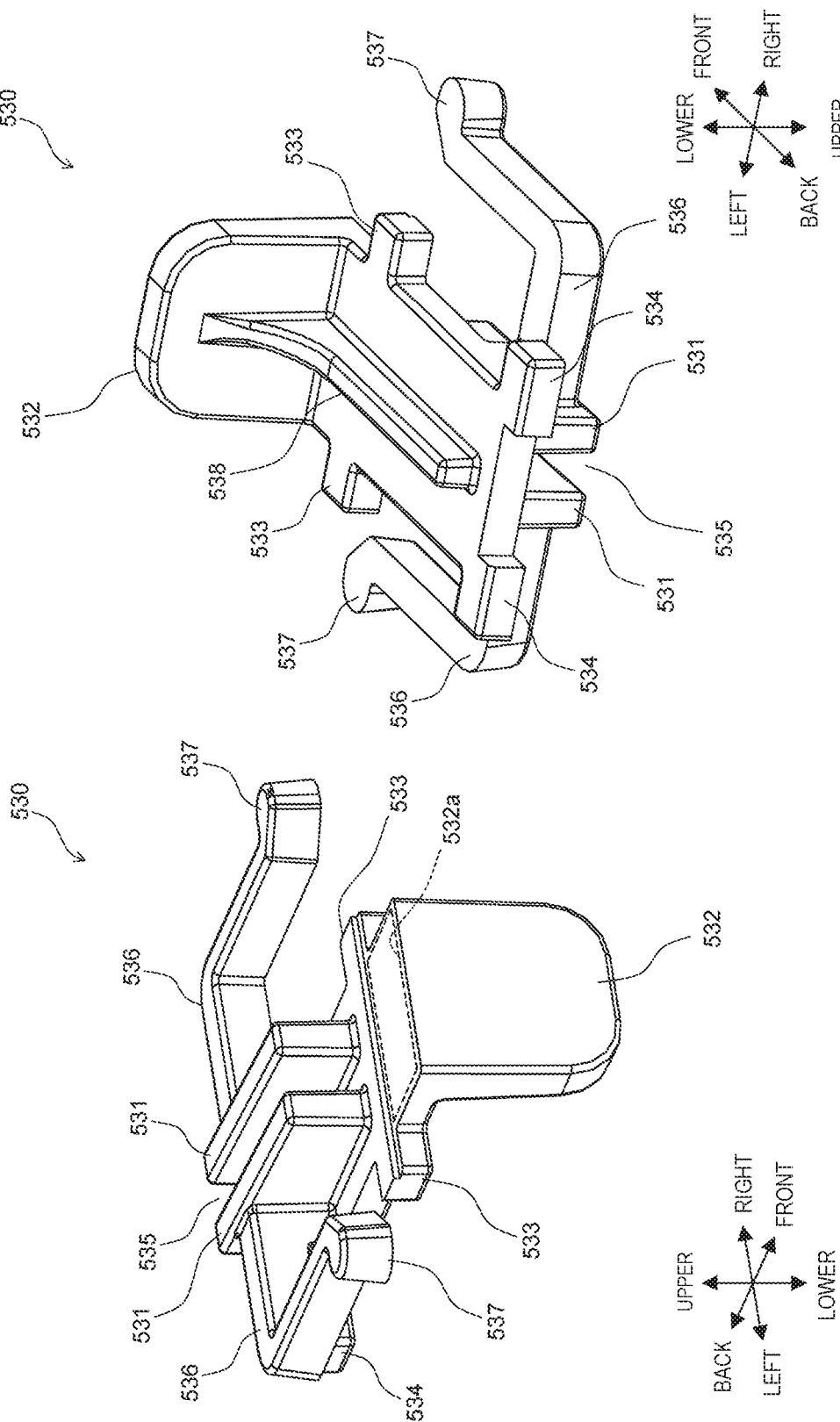

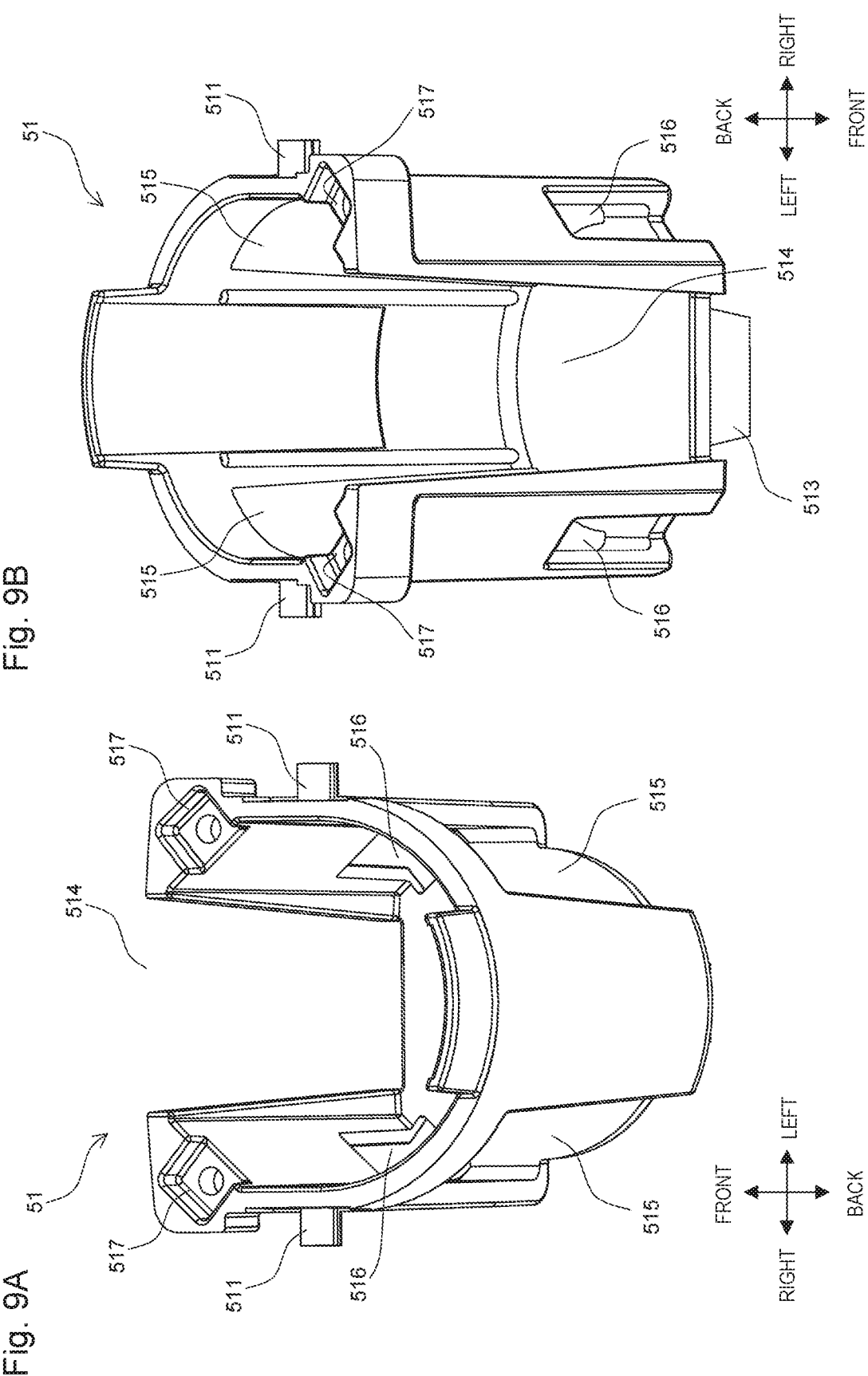

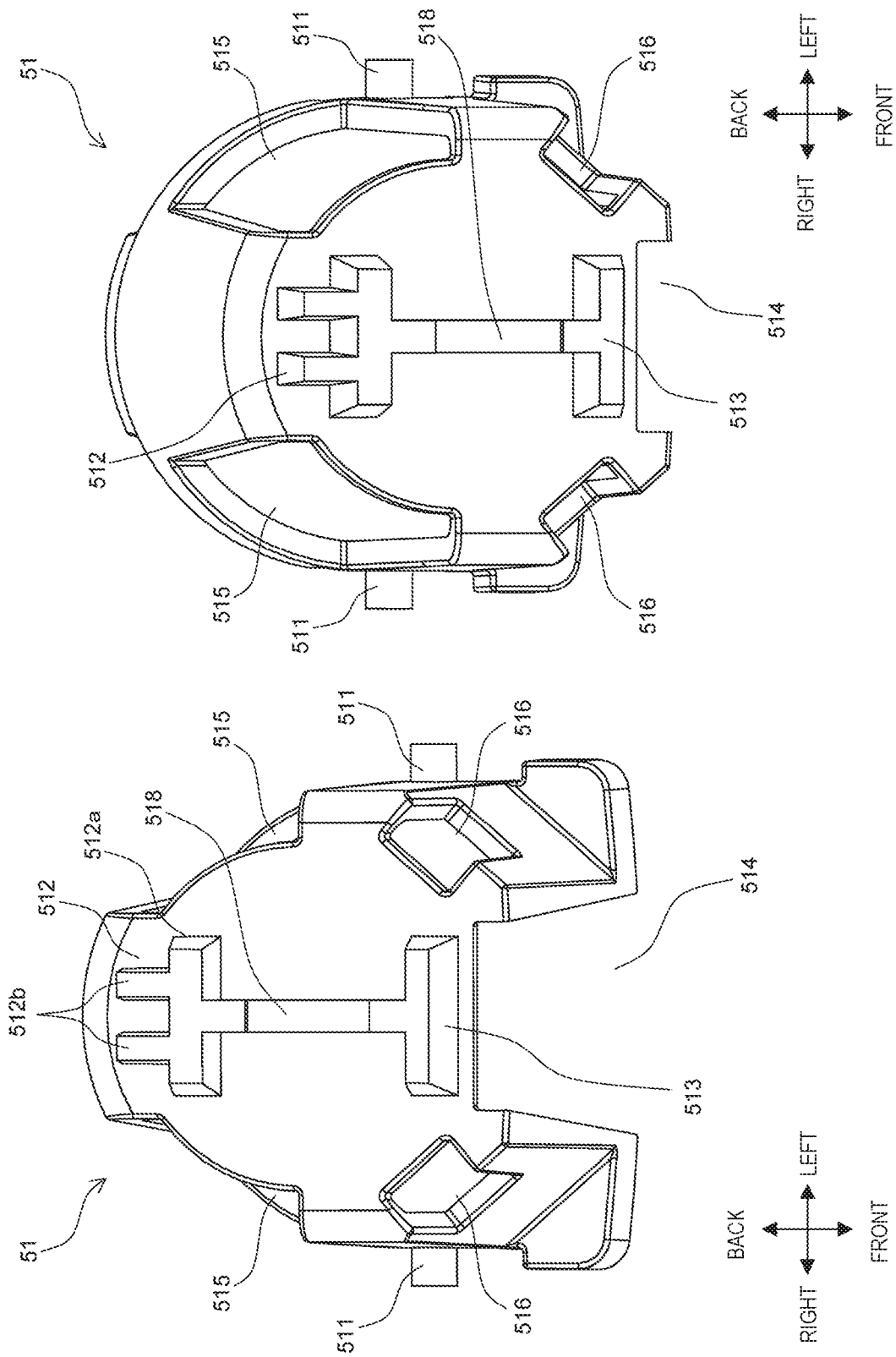
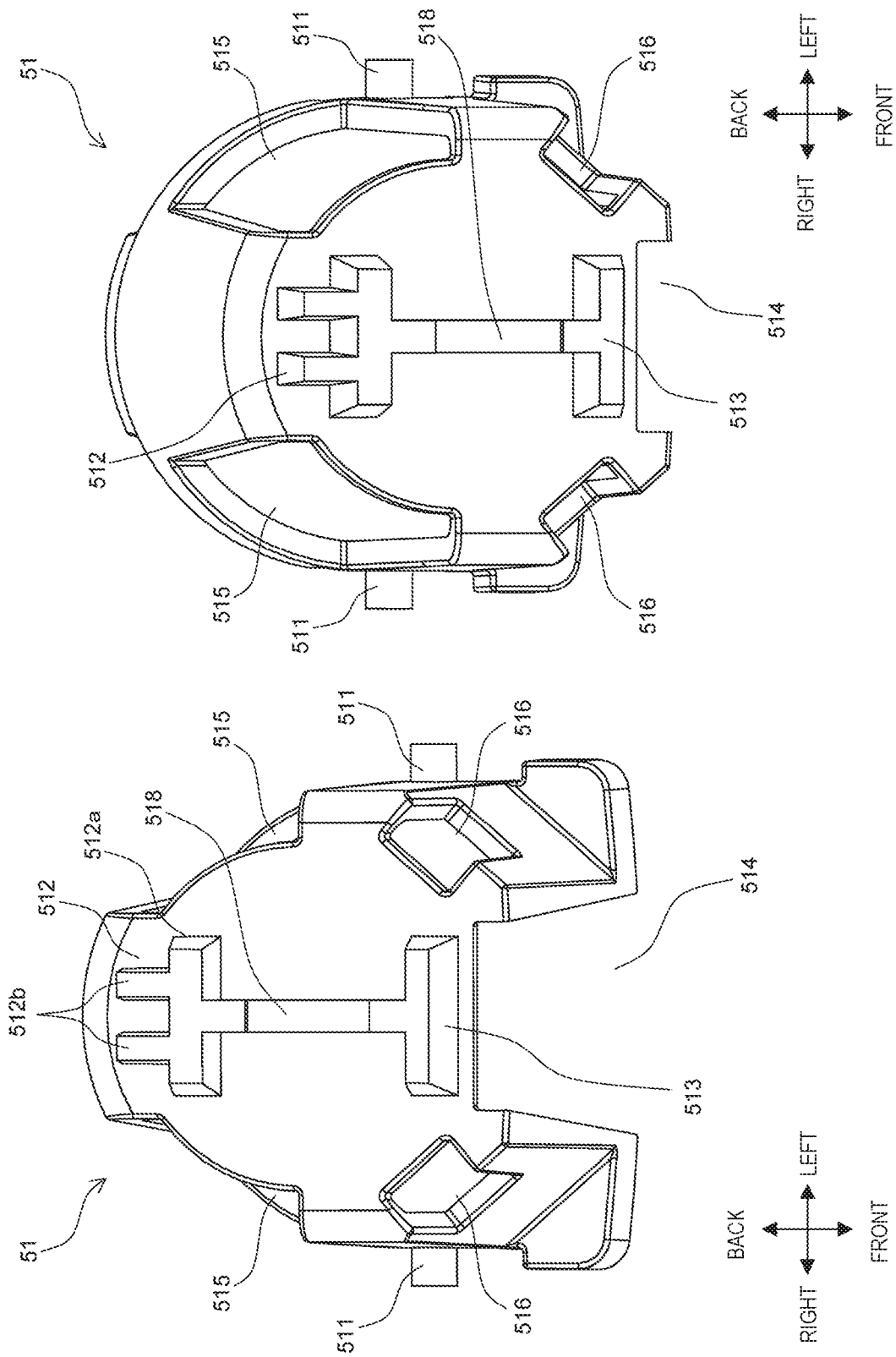

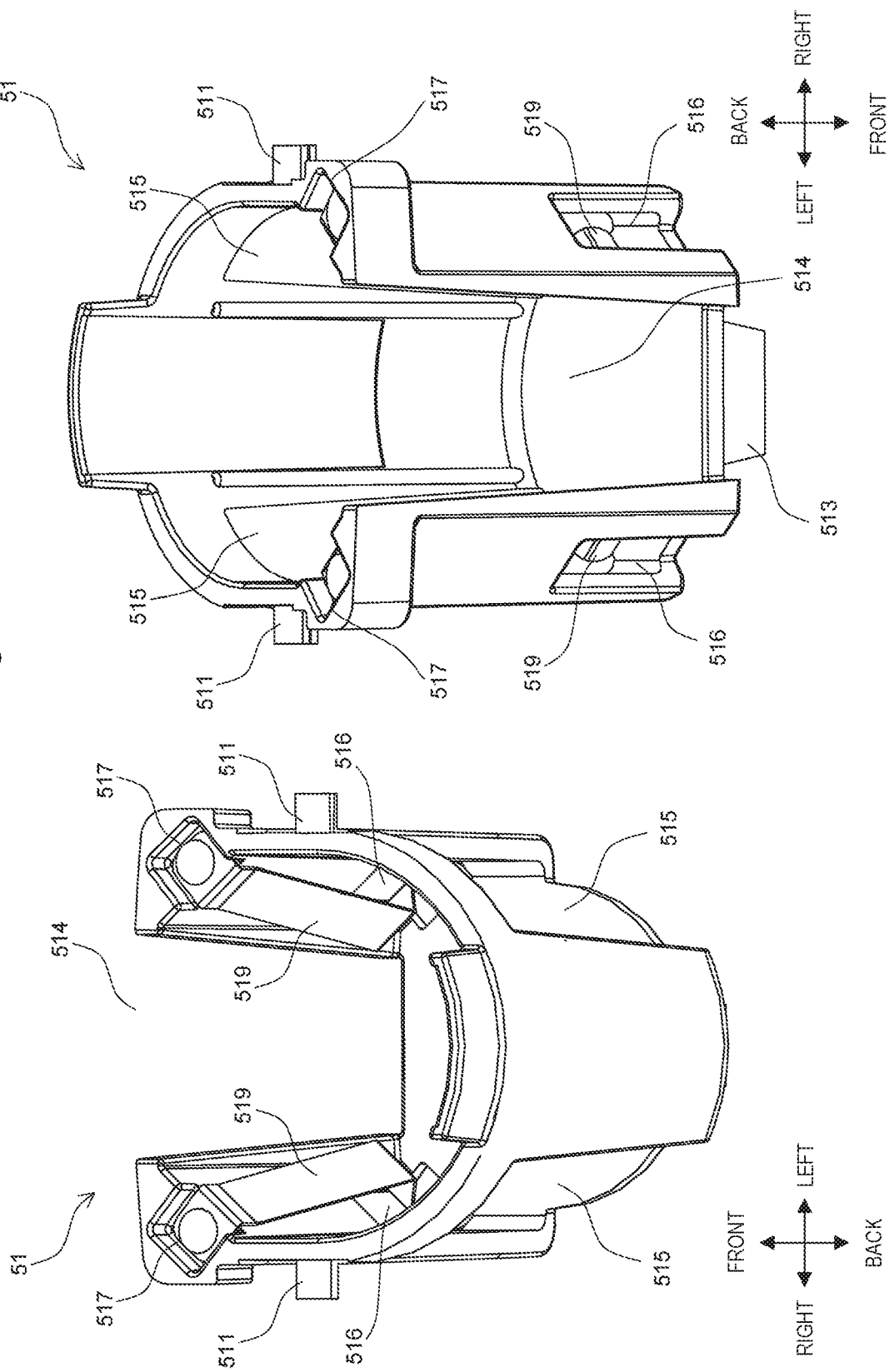

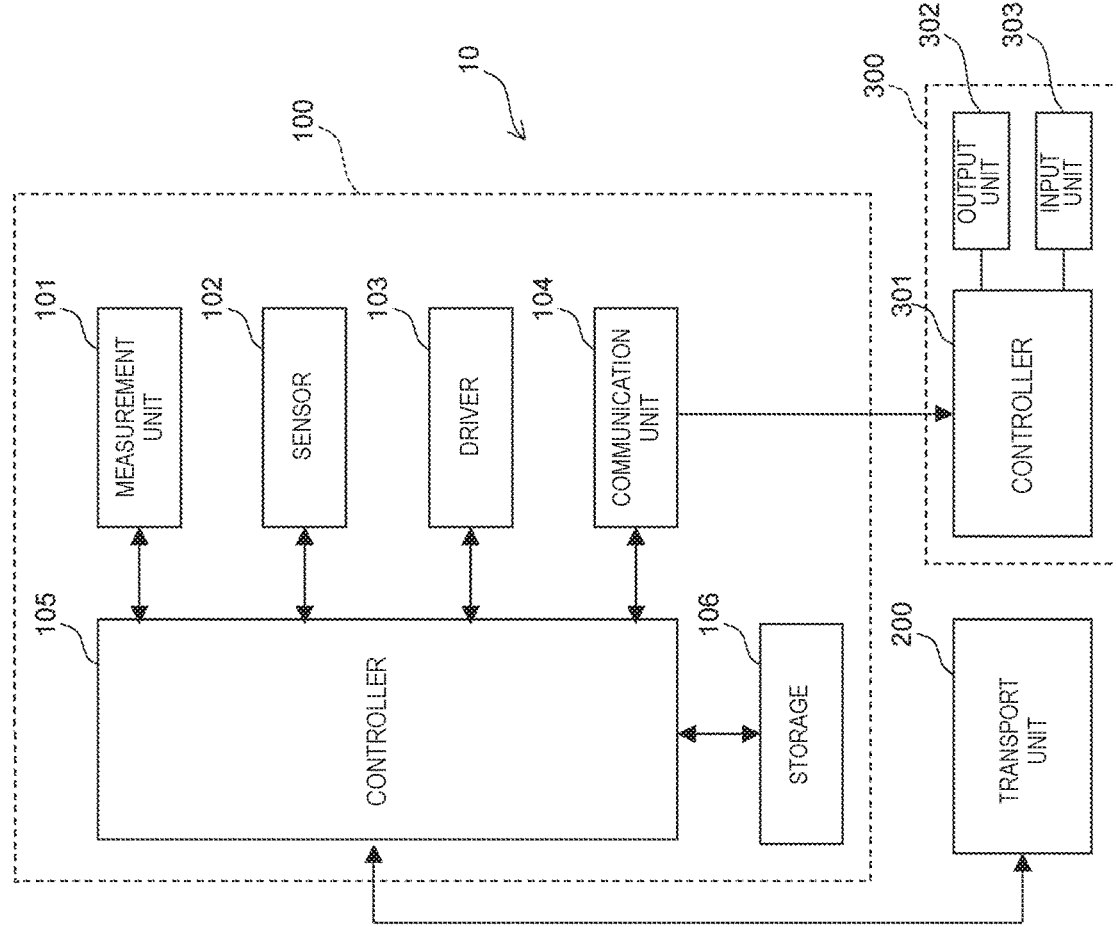

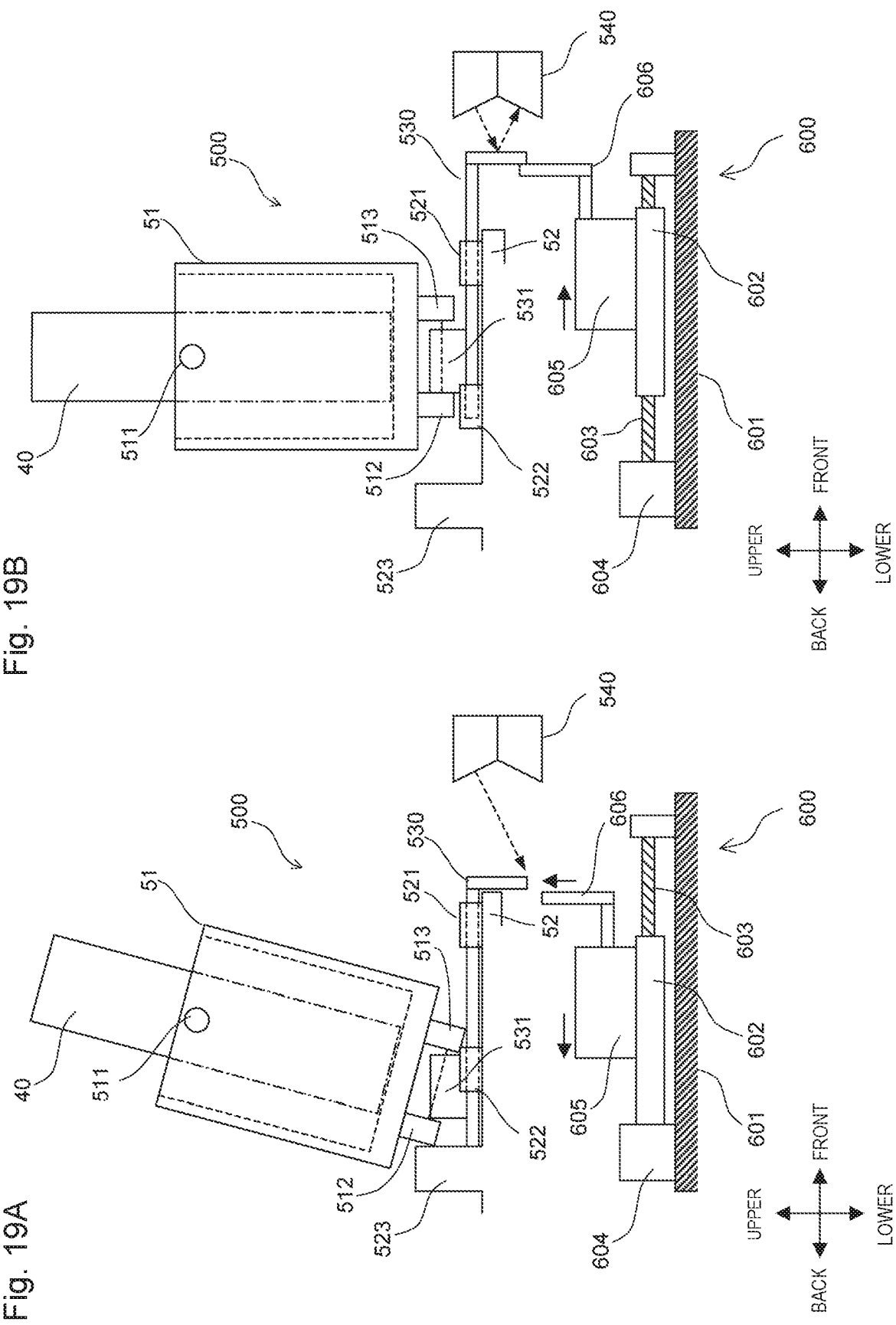

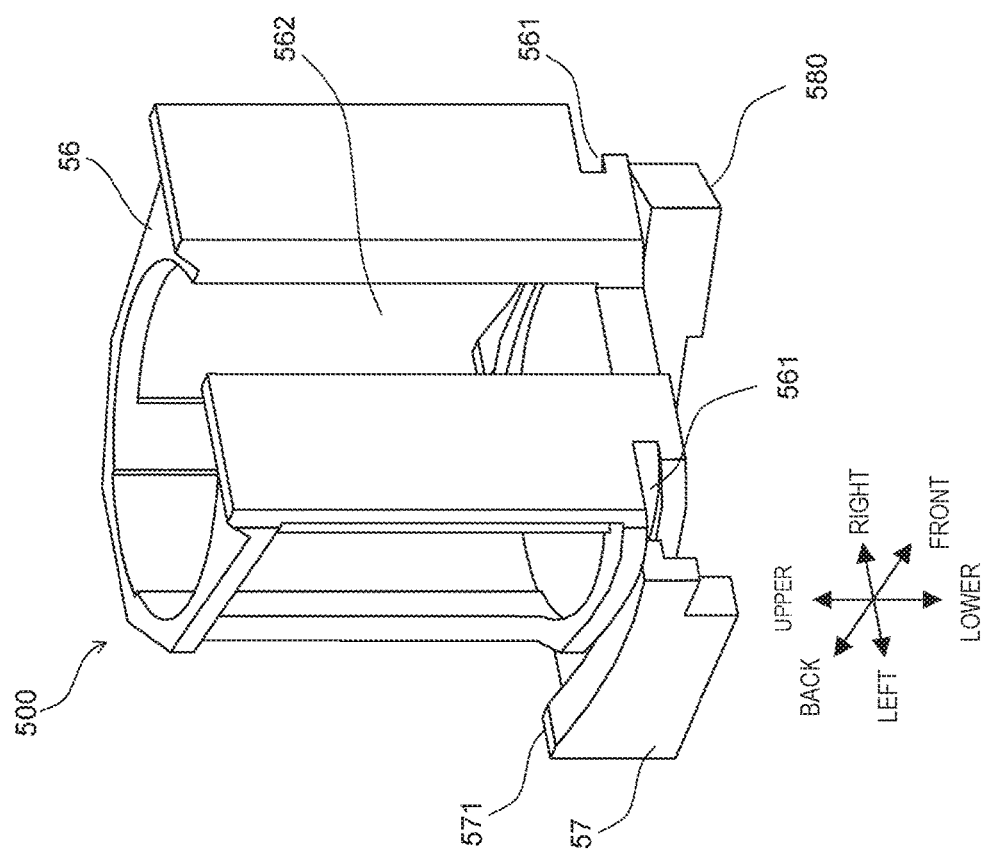
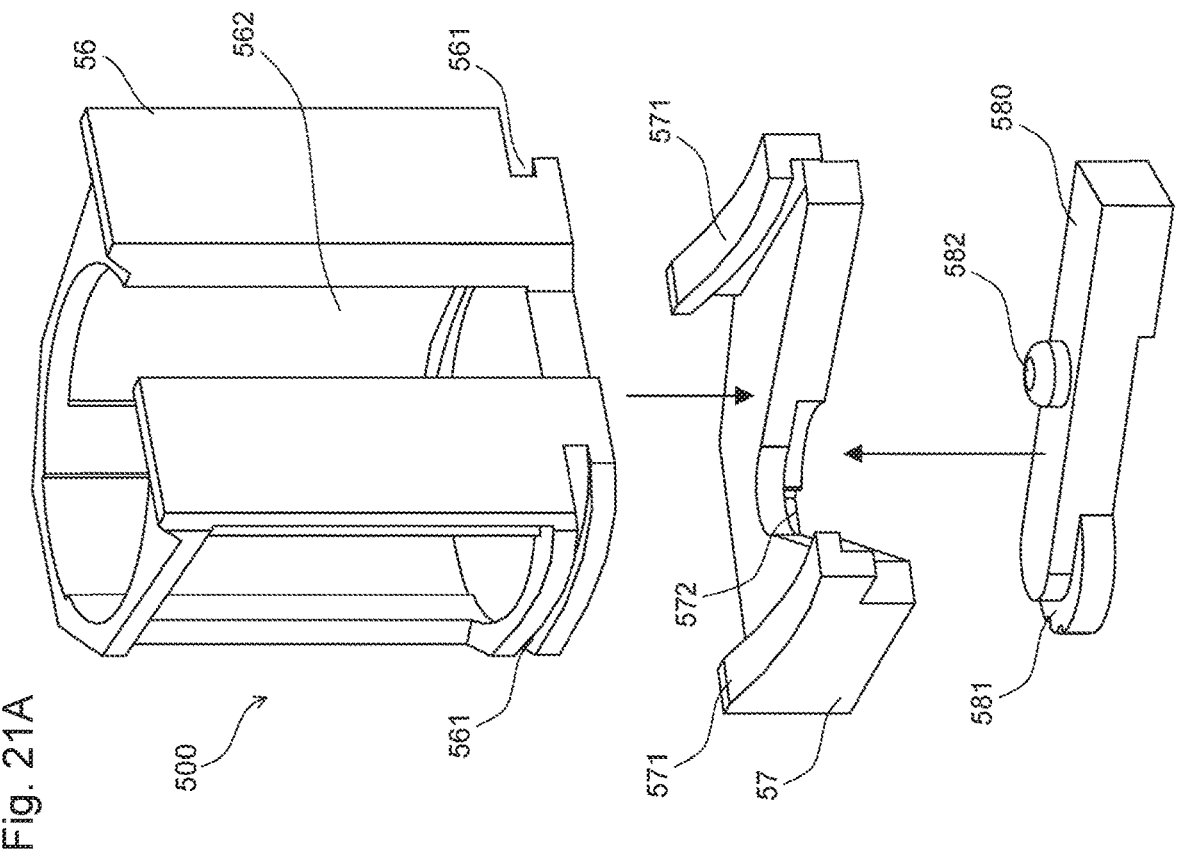

SAMPLE ANALYZER, SAMPLE ANALYZING METHOD, AND REAGENT CONTAINER HOLDER

CROSS REFERENCE TO RELATED APPLICATIONS

This application is a continuation of application Ser. No. 15/379,549, filed on Dec. 15, 2016, which is based upon and claims priority under 35 U.S.C. § 119 from prior Japanese Patent Application No. 2015-246614 filed on Dec. 17, 2015, entitled "SAMPLE ANALYZER AND SAMPLE ANALYZING METHOD", the entire contents of all of which are hereby incorporated herein by reference.

BACKGROUND

The disclosure relates to a sample analyzer, a sample analyzing method, and a reagent container holder for analyzing a specimen prepared by mixing a sample and a reagent.

The sample analyzer has been known which analyzes specimens prepared by mixing samples with reagents. The reagents are contained in reagent containers, and the reagent containers are held at predetermined places in the sample analyzer. The sample analyzer prepares the specimens by using the reagents in the held reagent containers. Since the reagents are expensive, it is desirable to reduce as much as possible the volumes of the reagents unused and left in the reagent containers, in short, dead volumes.

Japanese Patent Application Publication No. H11-295317 (Patent Literature 1) discloses a configuration in which a sample analyzer holds reagent containers at a tilt in order to completely aspirate reagents in the reagent containers without leaving the reagents. This sample analyzer includes holders for holding the reagent containers. Surfaces of the holders on which to mount the reagent containers are tilted such that the reagent containers can be set at a tilt.

SUMMARY

One or more embodiments of a sample analyzer may comprise a reagent container holder including a reagent container holder body configured to hold a reagent container, and a tilt changing part configured to change a tilt of the reagent container holder body; a reagent dispenser configured to aspirate a reagent contained in the reagent container held in the reagent container holder body; a detector configured to detect a signal for analysis from a measurement specimen containing a sample and the reagent dispensed by the reagent dispenser; and a controller that analyzes the sample on the basis of the signal detected by the detector.

One or more embodiments of a sample analyzing method may comprise changing, by a tilt changing part, a tilt of a reagent container holder body in a reagent container holder, wherein the reagent container holder includes: the reagent container holder body configured to hold a reagent container; and the tilt changing part configured to change the tilt of the reagent container holder body; aspirating, by a reagent dispenser, reagent in the reagent container held in the reagent container holder tilted by the tilt changing part; detecting a signal for analysis from a measurement specimen containing a sample and the reagent dispensed by the reagent dispenser; and analyzing the sample on the basis of the detected signal.

One or more embodiments of a reagent container holder may comprise a reagent container holder body configured to hold a reagent container containing a reagent; and a tilt changing part configured to change a tilt of the reagent container holder body.

BRIEF DESCRIPTION OF DRAWINGS

FIG. 1A is a schematic plan view illustrating a configuration of a sample analyzer according to an embodiment. FIGS. 1B and 10 are schematic side views illustrating a configuration of a tilt changing part according to an embodiment.

FIGS. 3A and 3B are schematic side views illustrating an aspiration operation in a case where a reagent container with a low height and large diameter is mounted and is tilted by the tilt changing part according to an embodiment. FIGS. 3C and 3D are schematic side views illustrating an aspiration operation in a case where a reagent container with a high height and small diameter is mounted and is tilted by the tilt changing part according to an embodiment.

FIG. 6A is a perspective view of an adapter according to an embodiment viewed from the upper front side. FIG. 6B is a perspective exploded view of the adapter according to an embodiment viewed from the upper front side.

FIG. 8A is a perspective view of a lever according to an embodiment viewed from the upper front side. FIG. 8B is a perspective view of the lever viewed from the upper back side, the lever turned upside down from the state in FIG. 8A.

FIG. 9A is a perspective view of a reagent container holder body according to an embodiment viewed from the upper back side. FIG. 9B is a perspective view of the reagent container holder body according to an embodiment viewed from the upper front side.

FIG. 10A is a perspective view of the reagent container holder body according to an embodiment viewed from a lower front side. FIG. 10B is a perspective view of the reagent container holder body according to an embodiment viewed from a lower back side.

FIG. 11A is a perspective view, viewed from the upper back side, of the reagent container holder body with a leaf spring attached thereto in an embodiment. FIG. 11B is a perspective view, viewed from the upper front side, of the reagent container holder body with the leaf spring attached thereto in an embodiment.

FIG. 16A is a block diagram illustrating a configuration of a sample analyzer according to an embodiment. FIG. 16B is a diagram illustrating a structure of a table stored in a storage and defining a relationship between a reagent container and a tilt according to an embodiment.

FIGS. 19A and 19B are schematic side views each illustrating the configuration and an operation of the driver that drives the tilt changing part in an embodiment

FIG. 21A is a perspective exploded view of a tilt changing part according to an embodiment viewed from the upper front side. FIG. 21B is a perspective view of the tilt changing part according to an embodiment viewed from the upper front side.

EMBODIMENTS

Figure 2A:
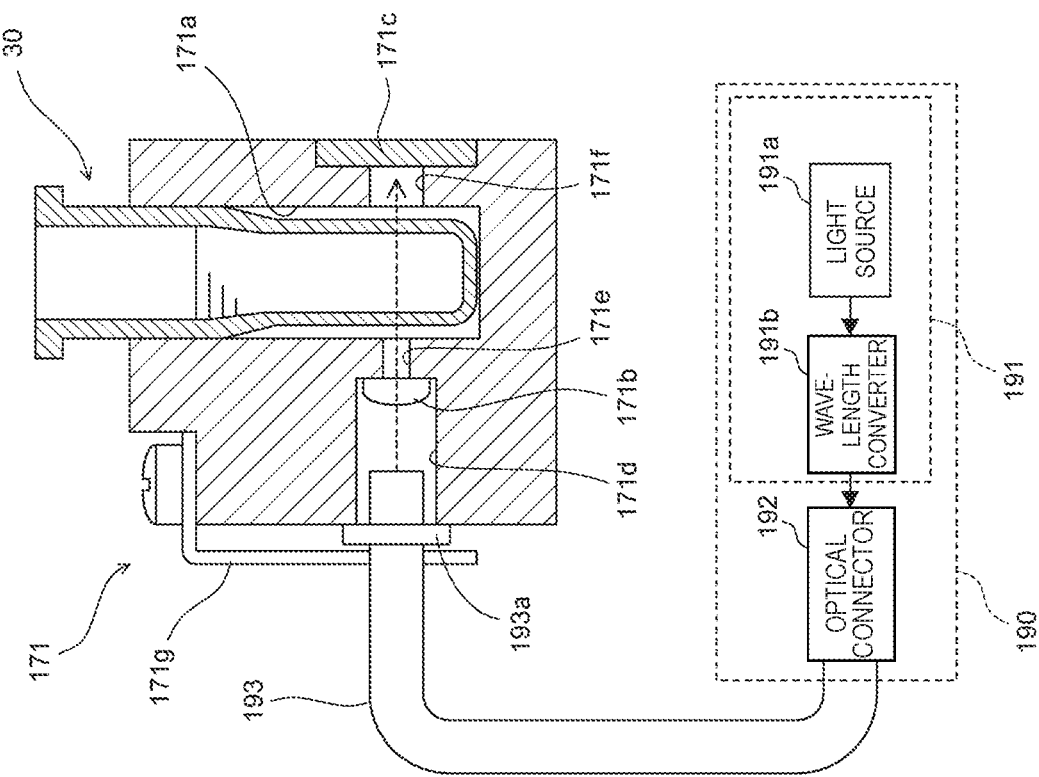
FIGS. 2A and 2B are schematic views illustrating a cross sectional configuration of a detector and a configuration of a light emission unit according to an embodiment.

A sample analyzer of this embodiment is a blood coagulation analyzer which analyzes blood coagulability by irradiating with light a measurement specimen prepared by adding a reagent to a sample, and analyzing the obtained transmitted light with a coagulation method, a synthetic substrate method, an immunonephelometry, or an agglutination method. In the case of a blood coagulation analyzer, various types of reagent containers containing reagents produced by various manufacturers are set in the analyzer. For this reason, the disclosure is preferably applicable to a blood coagulation analyzer. It should be noted, however, that sample analyzers to which the disclosure is applied are not limited to the blood coagulation analyzers, but may be any sample analyzer with another method as long as reagent containers are mounted in the analyzer.

Embodiment 1

As illustrated in FIG. 1A, sample analyzer 10 according to Embodiment 1 includes measurement unit 100, transport unit 200, and information processing unit 300. In FIG. 1A, XY axes are orthogonal to each other.

Transport unit 200 is arranged at a Y-axis negative side of measurement unit 100. Transport unit 200 includes rack set section 201, transport path 202, and rack collection section 203. In addition, transport unit 200 includes barcode reader 210 in transport path 202. Rack set section 201 and rack collection section 203 both connect with transport path 202.

A user mounts sample rack 21, in which sample containers 22 are set, on rack set section 201 of transport unit 200. A barcode is placed on sample rack 21, and barcodes are also placed on respective sample containers 22. Transport unit 200 transports sample rack 21 mounted on rack set section 201 to an end of transport path 202 on an X-axis negative side, and further transports sample rack 21 to a position where barcode reader 210 can read the barcodes. Barcode reader 210 reads the barcode placed on sample rack 21, and also the barcodes placed on sample containers 22.

The barcode of sample rack 21 holds a rack ID containing identification information for identifying sample rack 21. The barcode of each sample container 22 holds a sample ID containing identification information for identifying a sample contained in sample container 22. The rack ID and the sample IDs are transmitted to information processing unit 300 in order that information processing unit 300 can set measurement items for the samples.

Thereafter, transport unit 200 transports sample containers 22 held in sample rack 21 one after another to aspirating position 221. At aspirating position 221, the sample is aspirated from sample container 22. Transport unit 200 transports sample rack 21 to rack collection section 203 after the completion of sample aspiration from all sample containers 22 held in sample rack 21.

Measurement unit 100 aspirates the sample from sample container 22 at aspirating position 221, mixes the aspirated sample with a reagent, and performs measurement thereon. Measurement unit 100 transmits a measurement result of each sample to information processing unit 300. Information processing unit 300 includes controller 301. Controller 301 analyzes the sample on the basis of the measurement result received from measurement unit 100, and outputs the analysis result to an output unit such as a monitor.

Measurement unit 100 includes sample dispenser 110, reagent table 120, reaction container holder table 130, barcode reader 140, heater table 150, reagent dispensers 161, 162, detection unit 170, and reaction container feeder 180.

Sample dispenser 110 includes pivotable sample dispensing aim 112 and aspiration tube 111 provided at an end of sample dispensing arm 112.

Reagent table 120 has a circular outline in plan view, and is driven to rotate in a circumferential direction. As for reagent table 120, three reagent container holders 50 are detachably mounted on an outer circumferential side of reagent table 120, whereas four reagent container holders 60 are detachably mounted on an inner circumferential side of reagent table 120. Each reagent container holder 50 includes reagent container holder bodies 51 for holding reagent containers 40. The reagent containers held in reagent container holders 50, 60 have barcodes placed thereon. The barcode of each reagent container holds a container ID containing reagent container information such as the kind of reagent contained in the reagent container, the type of the reagent container, and the use-by date of the reagent. The barcode placed on the reagent container is read by barcode reader 140. The type of the reagent container is identified according to the type of the reagent container read by the barcode reader 140.

Reaction container holder table 130 has a ring shape in plan view, and is arranged outside reagent table 120. Reaction container holder table 130 is also driven to rotate in the circumferential direction. Reaction container holder table 130 and reagent table 120 are driven individually. Reaction container holder table 130 includes container retainers 131.

Container retainers 131 are arranged in equal pitches in the circumferential direction. Reaction containers 30 fed from reaction container feeder 180 are set in container retainers 131. Reaction containers 30 are cuvettes.

Barcode reader 140 reads the barcodes of the reagent containers set on reagent table 120. As illustrated in FIG. 1A, reagent container holders 50 on the outer circumferential side are set on reagent table 120 with spaces interposed in between in the circumferential direction. Through these spaces, barcode reader 140 reads the barcodes of the reagent containers held in reagent container holders 60 set on the inner circumferential side of reagent table 120.

Heater table 150 has a circular outline in plan view, and is driven to rotate in a circumferential direction. Heater table 150 includes heating sections 151. Heating sections 151 are arranged in equal pitches in the circumferential direction. Moreover, heater table 150 includes a catcher 152 for transporting reaction container 30 held in container retainer 131 of the reaction container holder table 130 to heating section 151.

Reagent dispensers 161, 162 each aspirate the reagent from a reagent container held on reagent table 120 and dispense the aspirated reagent into reaction container 30 in which the sample is contained. Each of reagent dispensers 161, 162 is installed on a support frame above the reagent table 120. Reagent dispensers 161, 162 include aspiration tubes 165, 166, respectively, for aspirating the reagent as illustrated in FIGS. 3A to 3D.

Aspiration tube 165 of reagent dispenser 161 is movable between reagent table 120 and dispensing position 163, whereas aspiration tube 166 of reagent dispenser 162 is movable between reagent table 120 and dispensing position 164. Aspiration tubes 165, 166 are moved in a vertical direction for the aspiration of the reagent. After the aspiration of the reagent from a reagent container, reagent dispenser 161 transfers aspiration tube 165 to dispensing position 163 and dispenses the aspirated reagent into reaction container 30 at dispensing position 163. After the aspiration of the reagent from a reagent container, reagent dispenser 162 transfers aspiration tube 166 to dispensing position 164 and dispenses the aspirated reagent into reaction container 30 at dispensing position 164. Reagent dispenser 161 is used to dispense a trigger reagent, and reagent dispenser 162 is used to dispense a primary reagent.

Instead of reagent dispensers 161, 162, other reagent dispensers may be provided in each of which an aspiration tube is arranged at an end of a pivotable aim, as is the case with sample dispenser 110. In this case, the reagent dispenser also includes an aspiration tube, and the aspiration tube of the reagent dispenser is moved in the vertical direction for the aspiration of a reagent.

Detection unit 170 includes detectors 171, catcher 172, and waste vent 173. Each of detectors 171 has a cavity for setting reaction container 30, and acquires a signal for analysis by irradiating with light reaction container 30 set in that cavity. Specifically, detector 171 receives, at a light receiver, light transmitted through reaction container 30, and outputs a detection signal based on the detection light thus received. As described above, the detection signal obtained by detector 171 is outputted to and then analyzed by information processing unit 300.

Figure 2B:
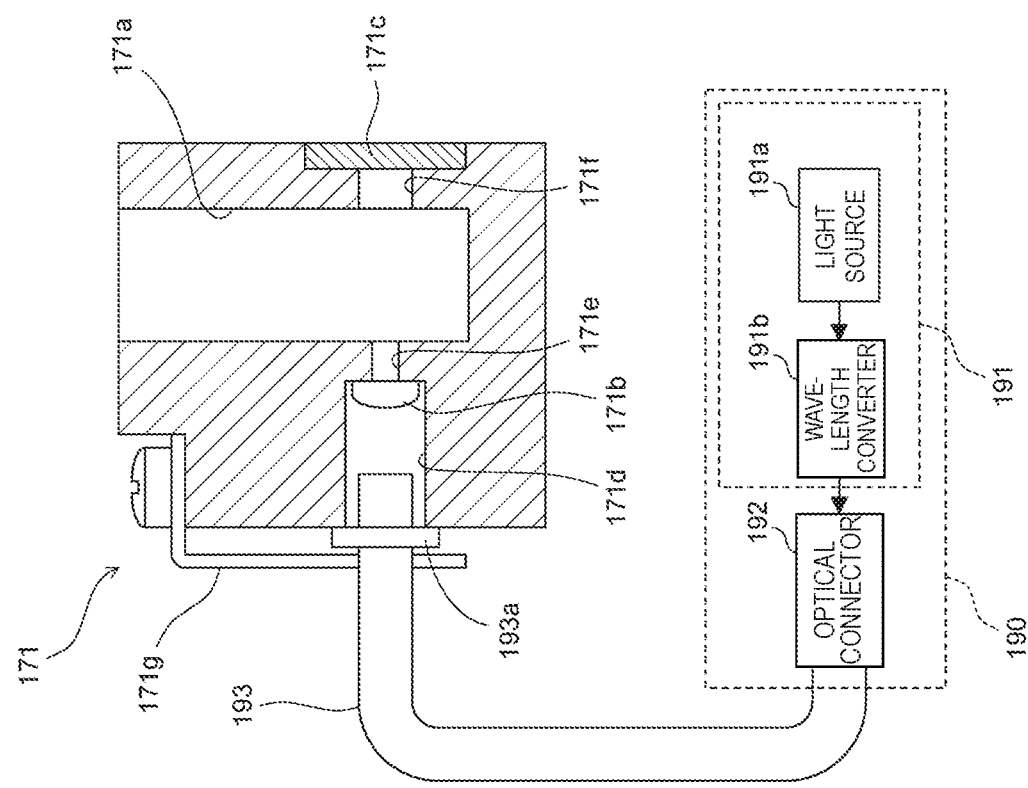

As illustrated in FIGS. 2A and 2B, detector 171 includes: specimen container hold section 171a for holding reaction container 30; light irradiation section 171b for irradiating with light reaction container 30 held in specimen container hold section 171a; light emission unit 190 which supplies light to light irradiation section 171b; and photosensor 171c which receives light transmitted through a specimen. Light irradiation section 171b is formed of a condenser lens, and is attached to circular hole 171d on a specimen container hold section 171a side. Hole 171d and specimen container hold section 171a communicate with each other through slot 171e. Light condensed by light irradiation section 171b is guided to reaction container 30 through slot 171e. Light irradiation section 171b may include another optical element such as a collimator lens in addition to the condenser lens.

Slot 171f is provided through which photosensor 171c and specimen container hold section 171a communicate with each other. Light condensed by light irradiation section 171b is transmitted through reaction container 30 and the specimen, and then is condensed on photosensor 171c. Photosensor 171c outputs a signal depending on the intensity of received light to information processing unit 300 illustrated in FIG. 1A. Controller 301 of information processing unit 300 analyzes the specimen on the basis of a variation with time in signals outputted from photosensor 171c. For example, on the basis of the signals outputted from photosensor 171c, controller 301 calculates certain values such as absorbance and turbidity of the specimen, and a time period it takes for the absorbance to reduce to a predetermined threshold.

Light emission unit 190 includes light source part 191, optical connector 192, and optical fiber 193. Light source part 191 includes light source 191a and wavelength converter 191b. In FIGS. 2A and 2B, components of the optical system other than light source part 191 and optical connector 192 are omitted from illustration for the sake of convenience.

Light source 191a includes a light emission lamp such as a halogen lamp. Wavelength converter 191b includes a filter unit such as a color wheel. Wavelength converter 191b converts light emitted from light source 191a into light with various wavelengths in a time-divided manner. For example, wavelength converter 191b outputs light with five wavelengths in a time-divided manner. Thus, light source part 191 repeatedly outputs the light with five wavelengths in a predetermined order. The light with wavelengths outputted from light source part 191 is sent to optical fiber 193 via optical connector 192.

End portion 193a of optical fiber 193 is inserted into hole 171d. The back side of end portion 193a is pressed by leaf spring 171g, and thereby end portion 193a is fixed to hole 171d. Light is supplied from light emission unit 190 to light irradiation section 171b via optical fiber 193. As described above, light irradiation section 171b is supplied with light with several wavelengths in the time-divided manner by light emission unit 190. Controller 301 generates time-series data of light with each wavelength based on the signals outputted from photosensor 171c. Then, controller 301 analyzes the sample on the basis of the time-series data thus generated. Specifically, controller 301 analyzes the sample by analyzing a specimen for each predeteimined measurement item on the basis of the signals outputted from photosensor 171c in response to the light with a wavelength for the predeteimined measurement item.

For instance, in the coagulation time method, the specimen is irradiated with light with a wavelength of 660 nm emitted from light source part 191, in other words, light for blood coagulation time measurement. Then, the light transmitted through the specimen is detected by photosensor 171c, whereby a time period it takes to transfoim fibrinogen to fibrin is analyzed. Measurement items of the coagulation time method are PT (prothrombin time), APTT (activated partial thromboplastin time), Fbg (fibrinogen), and so forth.

Meanwhile, in the synthetic substrate method, the specimen is irradiated with light with a wavelength of 405 nm emitted from light source part 191, in other words, light for synthetic substrate measurement, and the light transmitted through the specimen is detected by photosensor 171c. Measurement items of the synthetic substrate method are ATIII, α2-PI (α2-plasmin inhibitor), PLG (plasminogen), and so forth. Then, in the immunonephelometry, the specimen is irradiated with light with a wavelength of 800 nm emitted from light source part 191, in other words, light for immunonephelometry, and the light transmitted through the specimen is detected by photosensor 171c. Measurement items of the immunonephelometry are D dimer, FDP, and so forth. In the platelet agglutination method, the specimen is irradiated with light with a wavelength of 575 nm emitted from light source part 191, in other words, light for platelet agglutination measurement, and the light transmitted through the specimen is detected by photosensor 171c.

For example, controller 301 calculates the absorbance of the specimen on the basis of the detection signal outputted from photosensor 171c, and calculates, as a coagulation time of the specimen, a time period it takes for the calculated absorbance to exceed a predetermined threshold. Instead of the absorbance, controller 301 may obtain the turbidity on the basis of the detection signal, and calculate, as a coagulation time of the specimen, a time period it takes for the turbidity to exceed a predetermined threshold. Alternatively, controller 301 may calculate, as a coagulation time of the specimen, a time period it takes for the detection signal to exceed a predetermined threshold.

FIGS. 2A and 2B illustrate the configuration of detector 171 which detects light transmitted through a specimen. Instead, detector 171 may receive, at photosensor 171c, light scattered by a specimen and perform analysis in any of the foregoing methods based on the detection signal obtained from the scattered light. In this case, the layout of photosensor 171c and slot 171f is modified in detector 171. Specifically, photosensor 171c and slot 171f are arranged in a direction intersecting a traveling direction of light condensed by light irradiation section 171b, for example, in a direction orthogonal to the traveling direction of the light.

Returning to FIG. 1A, catcher 172 takes out reaction container 30 from heating section 151, and transfers reaction container 30 to dispensing position 163. In addition, catcher 172 transfers reaction container 30 to detector 171 after the reagent is dispensed into reaction container 30 at dispensing position 163. Moreover, catcher 172 takes out reaction container 30 after measurement from detector 171 and transfers reaction container 30 to waste vent 173.

Reaction container feeder 180 feeds each of reaction containers 30 stored in a storing section to a position where catcher 181 can hold reaction container 30. Catcher 181 transfers reaction container 30 thus fed to container retainer 131 of reaction container holder table 130, and sets reaction container 30 therein.

After transport unit 200 transports sample container 22 to aspirating position 221, sample dispenser 110 aspirates a sample from sample container 22, and dispenses the sample into empty reaction container 30 held in container retainer 131 of reaction container holder table 130. Reaction container holder table 130 transfers reaction container 30 with the sample dispensed therein to a pickup position near heater table 150. Catcher 152 of heater table 150 takes out reaction container 30 transferred to the pickup position, from reaction container holder table 130, and sets reaction container 30 in heating section 151 of heater table 150.

In the case of dispensing the primary reagent into reaction container 30, catcher 152 of heater table 150 transfers reaction container 30 heated by heater table 150 to dispensing position 164. Reagent dispenser 162 aspirates a reagent for primary dispensing from a predetermined reagent container held on reagent table 120, then dispenses the aspirated reagent into reaction container 30 transferred to dispensing position 164. Thereafter, catcher 152 again sets reaction container 30 in heating section 151.

When heating of reaction container 30 is completed, catcher 172 of detection unit 170 takes out reaction container 30 from heating section 151, and transfers reaction container 30, thus taken out, to dispensing position 163. Reagent dispenser 161 aspirates a reagent from a predetermined reagent container held on reagent table 120, and dispenses the aspirated reagent to reaction container 30 transferred to dispensing position 163. Thereafter, catcher 172 sets reaction container 30 in detector 171. Upon completion of a detection operation by detector 171, catcher 172 takes out reaction container 30 from detector 171, and transfers reaction container 30 to waste vent 173. Thus, reaction container 30 is discarded and the processing on the sample ends.

As illustrated in FIG. 1B, each reagent container holder 50 mounted on or detached from reagent table 120 includes tilt changing parts 500 each of which changes a tilt of corresponding reagent container holder body 51. Tilt changing parts 500 are respectively provided to all reagent container holder bodies 51 of reagent container holder 50. In Embodiment 1, tilt changing part 500 includes lever 530, engagement parts 531, guide parts 521, 522, a support unit, and a lock part. Engagement parts 531 are provided to lever 530, whereas guide parts 521, 522 are provided to support body 52.

Lever 530 and engagement parts 531 change the tilt of reagent container holder body 51. Guide parts 521, 522 smoothly move lever 530 between a third position and a fourth position to be described later. The support unit supports reagent container holder body 51 in a turnable manner. The lock part locks lever 530 at the third position and the fourth position to be described later. The support unit and the lock part in Embodiment 1 are described later in detail.

In FIG. 1B, a direction of a solid line arrow indicates a direction from the back side toward the front side of reagent container holder 50 and reagent container holder body 51. The direction from the back side toward the front side of reagent container holder 50 and reagent container holder body 51 corresponds to a direction from the center to the outside of reagent table 120. In the following drawings, the back side corresponds to the center side of reagent table 120, and the front side corresponds to the outside of reagent table 120 as in FIG. 1B.

Reagent container holder body 51 is turnable around shafts 511. Each shaft 511 extends in a direction intersecting a front-back direction that is a movement direction of lever 530. Protrusions 512, 513 are famed on a lower surface of reagent container holder body 51. Engagement parts 531 of lever 530 are placed between these protrusions 512, 513. Lever 530 is a plate-like member in an L-letter shape in side view. Lever 530 is movable linearly in a horizontal direction. Specifically, lever 530 is supported on support body 52 by way of guide parts 521, 522 such that lever 530 can move in the front-back direction of reagent container holder body 51. Moreover, support body 52 is provided with wall part 523 famed to face protrusion 512.

When lever 530 in the state in FIG. 1B is pushed in, engagement parts 531 push protrusion 512, and reagent container holder body 51 turns around shafts 511 as the central axis in a clockwise direction in the drawing. Lever 530 is pushed in until protrusion 512 hits wall part 523. In this way, reagent container holder body 51 is tilted just at a predetermined angle as illustrated in FIG. 10. When lever 530 in the state in FIG. 10 is moved frontward, engagement parts 531 push protrusion 513, and reagent container holder body 51 turns around shafts 511 as the central axis. Thus, reagent container holder body 51 returns to the state in FIG. 1B, in other words, an upright posture. The upright posture is a posture of reagent container holder body 51 in which central axis L0 of reagent container holder body 51 is parallel with the vertical direction.

Here, the position of reagent container holder body 51 in the upright posture as illustrated in FIG. 1B is referred to as a first position. Then, the position of reagent container holder body 51 by which reagent container 40 is held at a tilt, as illustrated in FIG. 10, compared to reagent container 40 held by reagent container holder body 51 placed at the first position is referred to as a second position. As explained with reference to FIGS. 1B and 10, tilt changing part 500 is configured to move reagent container holder body 51 between the first position and the second position.

The first position is not limited to the position of reagent container holder body 51 in the upright posture, but may be any position other than the position of reagent container holder body 51 in the upright posture as long as the tilt of reagent container 40 held by reagent container holder body 51 is smaller than in the case of the second position. Similarly, the second position is not limited to the position of reagent container holder body 51 illustrated in FIG. 10, but may be any position other than the position of reagent container holder body 51 illustrated in FIG. 10 as long as the tilt of reagent container 40 held by reagent container holder body 51 is larger than in the case of the first position.

Lever 530 is movable between the third position illustrated in FIG. 1B and the fourth position illustrated in FIG. 10. When lever 530 is placed at the third position with engagement parts 531 engaging with reagent container holder body 51, reagent container holder body 51 is placed at the first position. When lever 530 is placed at the fourth position with engagement parts 531 engaging with reagent container holder body 51, reagent container holder body 51 is placed at the second position.

In Embodiment 1, each engagement part 531 is constituted by a protrusion provided to lever 530, and this protrusion engages with reagent container holder body 51. However, engagement part 531 is not limited to this configuration, and just has to move along with a movement of lever 530 and engage with reagent container holder body 51. For example, engagement part 531 may include a protrusion provided to lever 530 and a member which brings the protrusion into engagement with reagent container holder body 51.

In Embodiment 1, guide parts 521, 522 are constituted by hook-shaped pieces provided to support body 52, and lever 530 is guided by these pieces to move between the third position and the fourth position as described later with reference to FIG. 7. However, guide parts 521, 522 are not limited to this configuration, and just have to guide the movement of lever 530 between the third position and the fourth position. For example, guide parts 521, 522 may include hook-shaped pieces provided to support body 52, and members arranged between these pieces and lever 530 and configured to guide lever 530.

In the case where reagent container 40 with a low height and large diameter is held in reagent container holder body 51 as illustrated in FIG. 3A, reagent container holder 50 is set on reagent table 120 in a state where reagent container holder body 51 is tilted with lever 530 pushed in, and the reagent in reagent container 40 is aspirated with aspiration tube 165 of reagent dispenser 161 or with aspiration tube 166 of reagent dispenser 162, as illustrated in FIG. 3B.

In the reagent aspiration operation, aspiration tube 165, 166 is moved down in the vertical direction and inserted into reagent container 40, and a tip end of aspiration tube 165, 166 is placed around the bottom of reagent container 40. After the aspiration with aspiration tube 165, 166 is teiminated, aspiration tube 165, 166 is moved up and taken out from reagent container 40.

In the aspiration operation, the reagent gathers around a corner of reagent container 40 if reagent container 40 with a low height and large diameter is tilted as illustrated in FIG. 3B. Then, the tip end of aspiration tube 165, 166 is placed around the corner of reagent container 40 where the reagent gathers. In this way, almost all the reagent contained in reagent container 40 can be aspirated with aspiration tube 165, 166. This makes it possible to analyze a sample by using reagents contained in various reagent containers while reducing the dead volumes of the reagents.

In the case where reagent container 40 with a high height and small diameter is held in reagent container holder body 51, lever 530 may be pushed in and reagent container holder body 51 may be tilted as illustrated in FIG. 3C. In this case, however, if aspiration tube 165, 166 is moved down in the vertical direction, the tip end of aspiration tube 165, 166 will hit the upper end of reagent container 40, and aspiration tube 165, 166 cannot be inserted to the inside of reagent container 40. For this reason, in the case where such reagent container 40 is set in reagent container holder body 51, it is necessary to keep reagent container 40 in the upright posture without tilting reagent container holder body 51 as illustrated in FIG. 3D.

Also in the case where reagent container 40 with a non-flat bottom or reagent container 40 with a conical bottom is held in reagent container holder body 51, lever 530 is operated to place reagent container holder body 51 in the upright posture or in the tilted posture depending on the shape of the bottom. Thereby, almost all the reagent contained in reagent container 40 can be aspirated with aspiration tube 165, 166. Therefore, the dead volume of the reagent can be reduced as well in this case.

In the case where reagent container 40 almost full with a reagent is held in reagent container holder body 51, the reagent in reagent container 40 may be spilled if reagent container holder body 51 is tilted with lever 530 pushed in. For this reason, in the case where such reagent container 40 is set in reagent container holder body 51, it is necessary to keep reagent container 40 in the upright posture without tilting reagent container holder body 51.

After setting reagent container 40 in reagent container holder body 51 of reagent container holder 50, the user determines whether or not to push lever 530 in depending on a type of reagent container 40 thus set, i.e., the height, the diameter, the shape of the bottom of reagent container 40, the volume of the reagent contained therein, and so forth.

For example, in the case where reagent container 40 with a low height and large diameter is set in reagent container holder body 51, the user pushes lever 530 in and tilts reagent container 40. In the case where reagent container 40 with a high height and small diameter is set in reagent container holder body 51, the user keeps reagent container 40 in the upright posture without pushing lever 530 in. In the case where reagent container 40 whose bottom is high in the center is set in reagent container holder body 51, the user pushes lever 530 in and tilts reagent container 40. Then, in the case where reagent container 40 whose bottom is high in the periphery is set in reagent container holder body 51, the user keeps reagent container 40 in the upright posture without pushing lever 530 in. In the case where reagent container 40 almost full with a reagent is set in reagent container holder body 51, the user keeps reagent container 40 in the upright posture without pushing lever 530 in.

After conducting tilting operations of all reagent container holder bodies 51 as described above, the user sets reagent container holder 50 on reagent table 120 illustrated in FIG. 1A.

Hereinafter, a specific configuration of reagent container holder 50 according to Embodiment 1 is explained with reference to FIGS. 4 to 14. In the following description, reagent container 40 set in reagent container holder body 51 is assumed to have a flat bottom and contain a small volume of a reagent.

Figure 4:
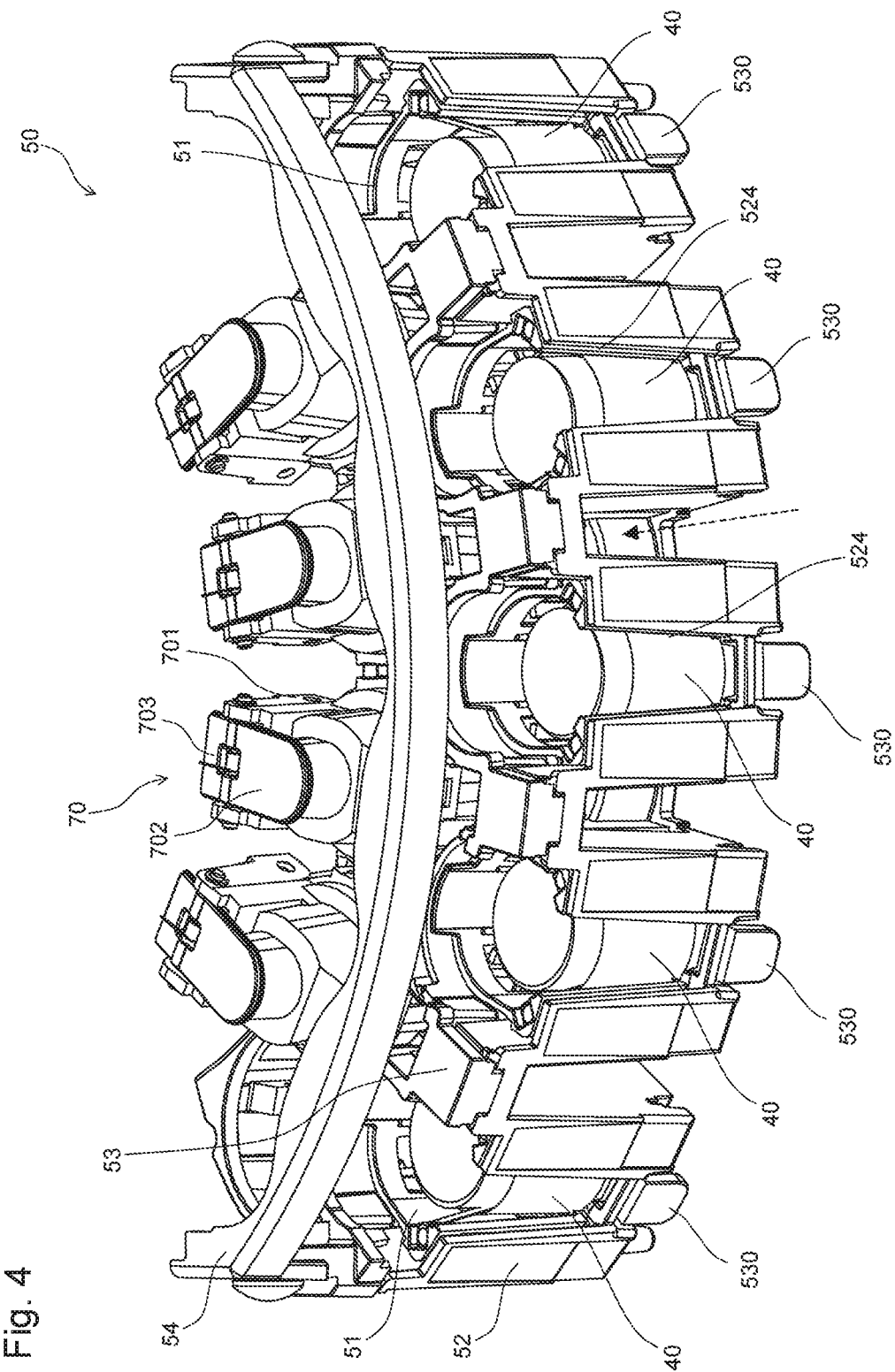
FIG. 4 is a perspective view of a reagent container holder according to an embodiment viewed from an upper front side.
Figure 5:
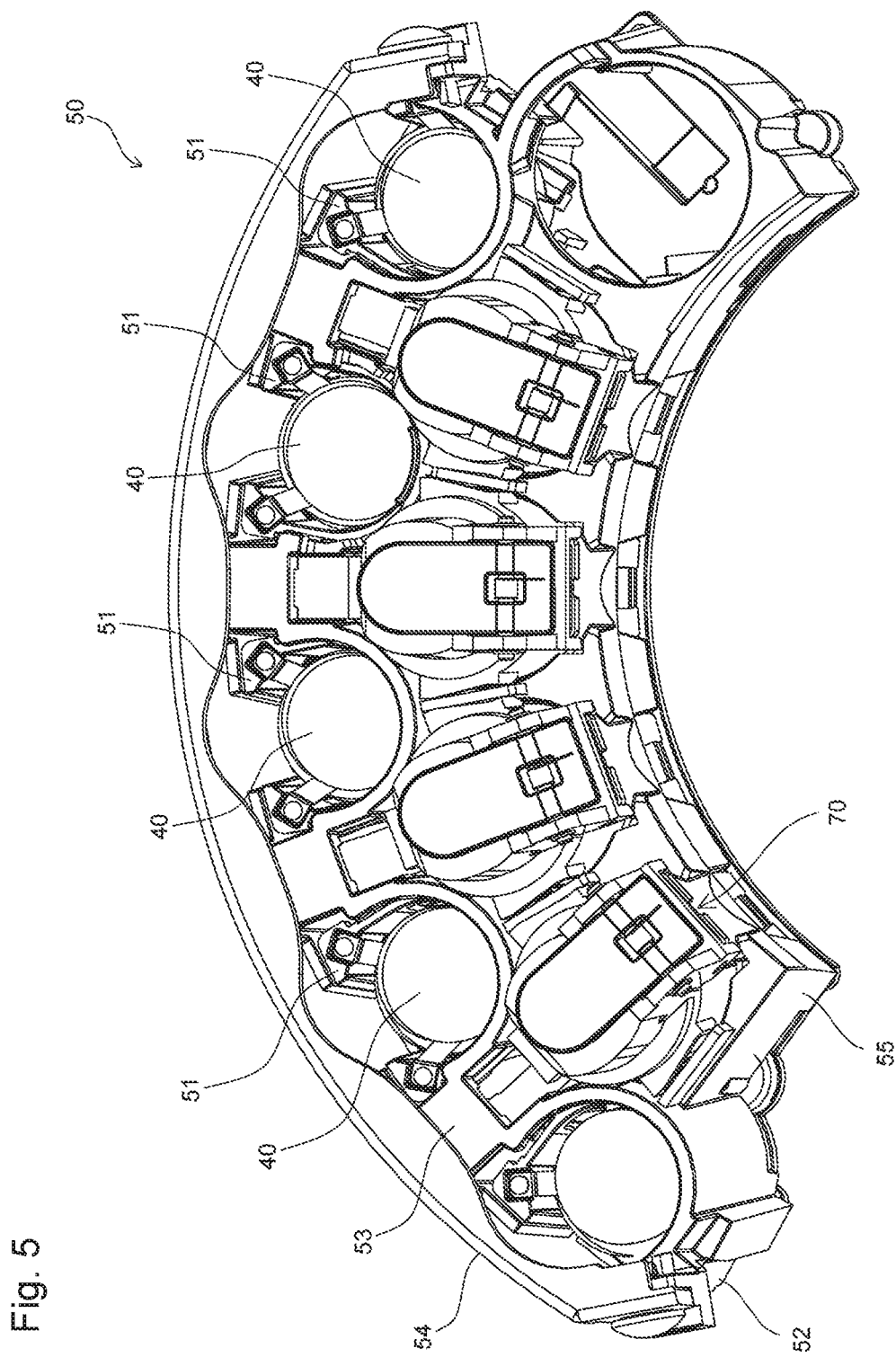
FIG. 5 is a perspective view of the reagent container holder according to an embodiment viewed from an upper back side.

As illustrated in FIGS. 4 and 5, reagent container holder 50 is configured to be capable of housing reagent containers 40 and adapters 70 in an arc-form arrangement in plan view. Reagent container holder 50 includes support body 52 as a base, cover 53 arranged on top of support body 52, handle 54 turnably supported by support body 52, and seat 55. Handle 54 is grabbed by the user when the user carries reagent container holder 50. Seat 55 includes openings for supporting adapters 70.

Five reagent container holder bodies 51 are supported to be turnable relative to support body 52 in such a way that shafts 511, illustrated in FIGS. 1B and 1C, are supported by support body 52. Five reagent container holder bodies 51 are capable of individually holding various reagent containers 40. Front portion of support body 52 reagent container holder bodyis cut out to faun openings 524. The barcode of each reagent container 40 is read through this opening 524. The user sets reagent container 40 in reagent container holder body 51 so that the barcode is exposed through opening 524. FIGS. 4 and 5 illustrate a state where reagent containers 40 with low heights and large diameters are held in respective reagent container holder bodies 51.

Lever 530 is placed at a position right below opening 524. FIG. 4 illustrates the state where all levers 530 are pulled out to the front side. Thus, none of reagent container holder bodies 51 is tilted, and all reagent containers 40 are in the upright posture. By pushing lever 530 in, the user can tilt corresponding reagent container 40. In the example of FIG. 4, reagent containers 40 with low heights and large diameters are held in respective reagent container holder body 51, and therefore the user tilts all reagent containers 40 by conducting push-in operations of all levers 530. Thereafter, the user sets reagent container holder 50 on reagent table 120, illustrated in FIG. 1A.

In FIGS. 4 and 5, four adapters 70 are set on the back side of support body 52. Adapter 70 holds a reagent container that contains, for example, a reagent which tends to easily evaporate and to affect a measurement result when the concentration thereof is changed due to evaporation. Adapter 70 is arranged in a state where an upper portion of adapter 70 is tilted at a predetermined angle from an upright posture to the front side of reagent container holder 50. In other words, seat 55 provided on support body 52 for adapter 70 is tilted from a horizontal plane just at a predetermined angle. As illustrated in FIG. 4, each adapter 70 is arranged behind a space between neighboring reagent container holder bodies 51. The barcode of the reagent container housed in adapter 70 is read through the space between neighboring reagent container holder bodies 51 as illustrated by a broken-line arrow in FIG. 4.

As illustrated in FIGS. 6A and 6B, adapter 70 includes main body 710 and cover 720. Main body 710 is a frame-shaped member capable of housing a reagent container. Cover 720 is turnably supported by main body 710 with holes 721 fit to shafts 711 formed in an upper portion of main body 710. When hole 722 provided at a front lower portion of cover 720 engages with lug 712 provided at a front upper portion of main body 710, cover 720 is kept in a closed state. Opening 713 is formed on the front side of main body 710. The barcode of a reagent container housed in adapter 70 is read through this opening 713.

Cover 720 has a cap-like structure and includes an opening 723 in an upper portion. Cover 720 is provided with lid 725 pivotable by way of shaft 724. Lid 725 is energized by spring 726 so as to close opening 723. Spring 726 is fit around shaft 724. Shaft 724 is kept from slipping off by washers 727.

In the case of mounting or removing a reagent container into or from adapter 70, the user disconnects the engagement of lug 712 and hole 722, and turns cover 720 around shafts 711. With this operation, the upper side of main body 710 is opened. The user pulls out a reagent container from above main body 710 or mounts a reagent container on the inside of main body 710 from above main body 710. After the reagent container is mounted, the user turns cover 720 in the closing direction. Thus, lug 712 and hole 722 engage with each other, so that cover 720 is closed.

In the case of aspirating a reagent from a reagent container housed in adapter 70, lid 725 is opened by a link mechanism provided to sample analyzer 10 but not illustrated, and aspiration tube 165 or aspiration tube 166 is inserted into the reagent container inside adapter 70. Upon termination of the reagent aspiration, the link mechanism is returned to close lid 725. Lid 725 is energized by spring 726 and is pressed against opening 723. This ensures that opening 723 is closed. By closing lid 725 in this way, the reagent is inhibited from evaporating, and a change in the concentration of the reagent is reduced.

Figure 7:
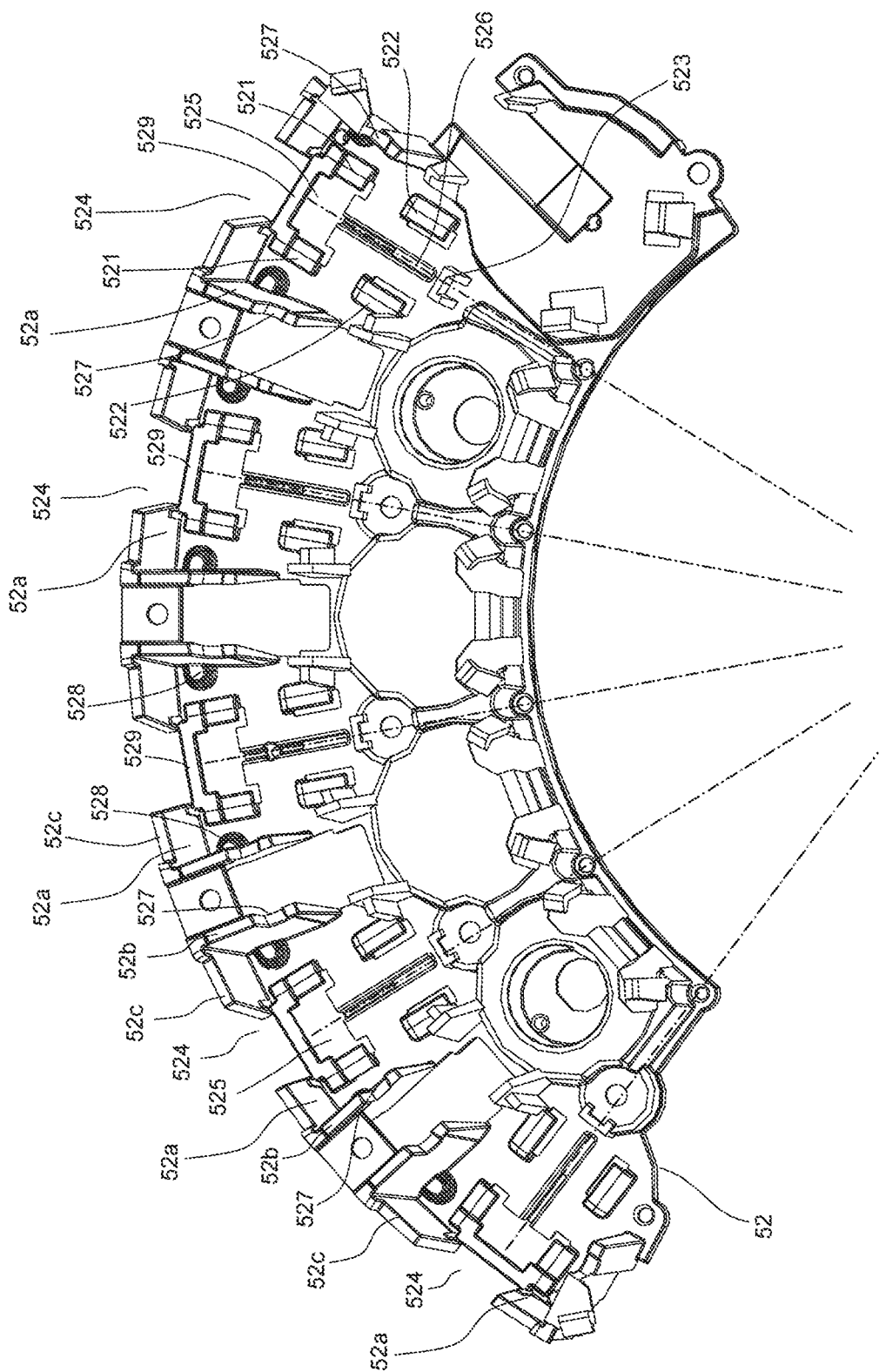
FIG. 7 is a perspective view of a support body according to an embodiment viewed from the upper back side.

In support body 52, five installation areas 52a for installing reagent container holder bodies 51 are arranged side by side in an arc shape as illustrated in FIG. 7. In FIG. 7, dashed-dotted lines each bisecting installation areas 52a in the circumferential direction are additionally drawn for the sake of convenience. The five dashed-dotted lines extend radially from the center of one arc sector in plan view. Each installation area 52a is demarcated by two walls 52b in the circumferential direction and is demarcated by wall 52c from the outside. Opening 524 is formed in wall 52c. Installation areas 52a have the same structure. Support body 52 is made of a resign material, for example.

Each installation area 52a is provided with hole 525, groove 526, bearings 527, bumps 528 and bridge part 529 in addition to guide parts 521, 522 and wall part 523 illustrated in FIGS. 1B and 10. Guide parts 521, 522 are the hook-shaped pieces raised upward from the bottom surface of installation area 52a. Wall part 523 is formed to have a groove 526 side surface vertical to the bottom surface of installation area 52a. Groove 526 is famed to extend along the dashed-dotted line from opening 524 to the vicinity of wall part 523.

Bearings 527 are formed in respective top surfaces of two walls 52b between which installation area 52a is sandwiched in the circumferential direction. Bump 528 in an arc shape in plan view is famed at a boundary of the bottom surface of installation area 52a with each of inner surfaces of two walls 52b between which installation area 52a is sandwiched. In plan view, bump 528 juts out in a mountain-like shape from the inner surface of wall 52b. In addition, bump 528 is raised in a mountain-like shape from the bottom surface of installation area 52a. There is a clearance between each bump 528 and wall 52c. Bridge part 529 is formed to connect the upper surfaces of two guide parts 521.

As illustrated in FIGS. 8A and 8B, lever 530 includes operation part 532, flange parts 533, flange parts 534, groove part 535, aim parts 536, tip end parts 537, and projection part 538 in addition to engagement parts 531 illustrated in FIG. 1B. Lever 530 is made of a flexible material such as a resin. In FIGS. 8A and 8B, arrows indicating the front, back, right, left, upper, and lower sides are additionally drawn for the sake of convenience. As described above, the back side corresponds to the center side of reagent table 120, and the front side corresponds to the outside of reagent table 120. Lever 530 has a symmetric shape in the right-left direction.

Each engagement part 531 protrudes in a plate shape upward from the upper surface of the main body of lever 530. On the upper surface of the main body of lever 530, two engagement parts 531 are formed to extend in the front-back direction while being parallel with each other. Two engagement parts 531 have equal lengths in the front-back direction. The heights of two engagement parts 531 are substantially constant and equal to each other. The widths of two engagement parts 531 are also substantially constant and equal to each other. Groove part 535 is formed between two engagement parts 531.

Operation part 532 is hung downward from the front end of the main body of lever 530. When lever 530 is pushed in toward the back side, the user presses the front side of operation part 532 with the finger. Meanwhile, when lever 530 is pulled out toward the front side, the user pulls lever 530 with the finger put on the back side of operation part 532.

Flange parts 533 jut from a front portion of the main body of lever 530 to the right and left, respectively. Flange parts 534 jut from a back portion of the main body of lever 530 to the right and left, respectively. In addition, arm parts 536 are famed on the left surface of left engagement part 531 and on the right surface of right engagement part 531. Arm parts 536 extend to the right and left, and then are bent to the front side. The lower surfaces of arm parts 536 are at higher positions than the upper surfaces of flange parts 533, 534, i.e., the upper surface of the main body of lever 530. Since lever 530 is made of the flexible material as described above, arm parts 536 are elastically deformable in the right-left direction.

Tip end parts 537 are famed at the tip ends of two aim parts 536, respectively. In plan view, each tip end part 537 has an arc shape. In other words, tip end part 537 has a side surface curved in an arc shape. Right tip end part 537 juts from right arm part 536 to the right, and left tip end part 537 juts from the tip end of left arm part 536 to the left.

Projection part 538 extending in the front-back direction is famed on the lower surface of the main body of lever 530. Projection part 538 is famed at the central position in the right-left direction on the lower surface of the main body of lever 530. The height of projection part 538 is constant from the back end to a point around flange parts 533, and gradually increases from the point around flange parts 533 to the front end. The width of projection part 538 in the right-left direction is substantially constant.

Mark area 532a in an upper surface of operation part 532 is provided with a mark in order that the user can easily visually check whether or not lever 530 is pushed in and placed at the fourth position. In Embodiment 1, a color is used as the mark. In the case where a color is used as the mark, a paint may be applied or a seal may be placed on mark area 532a. As the color used as the mark, for example, a red color, a yellow color, or the like may be selected so as to facilitate visual check by the user. Meanwhile, as a variation of the mark, mark area 532a may be mirror-finished or may be processed to cause diffused reflection.

As illustrated in FIGS. 9A, 9B, 10A and 10B, reagent container holder body 51 includes openings 514 to 516, recessed parts 517 and ridge 518 in addition to shafts 511 and protrusions 512, 513. Reagent container holder body 51 is a frame-shaped member capable of holding reagent container 40, and is made of a material such as a resin. In FIGS. 9A, 9B, 10A and 10B, arrows indicating the front, back, right, left sides are additionally drawn for the sake of convenience. As described above, the back side corresponds to the center side of reagent table 120, and the front side corresponds to the outside of reagent table 120. Reagent container holder body 51 has a symmetric shape in the right-left direction.

Two shafts 511 jut to the right and left, respectively, from an upper portion of the main body of reagent container holder body 51. Shafts 511 are arranged at the center of the main body of reagent container holder body 51 in the front-back direction.

Protrusions 512, 513 and ridge 518 are foamed on the lower surface of reagent container holder body 51. Protrusion 512 includes protrusion part 512a extending in the right-left direction and two protrusion parts 512b extending in the front-back direction. Two protrusion parts 512b have equal widths and lengths. Two protrusion parts 512b are arranged around a back end of the lower surface of reagent container holder body 51. Protrusion 513 is famed to extend in the right-left direction around a front end of the lower surface of reagent container holder body 51. Ridge 518 is foamed to extend in the front-back direction and to connect protrusions 512, 513 together. Ridge 518 is arranged at the central position of the lower surface of reagent container holder body 51 in the right-left direction. The height of ridge 518 is stepped down in a central portion.

Opening 514 is famed by cutting out a front side of reagent container holder body 51. The barcode of reagent container 40 held in reagent container holder body 51 is read through opening 514. Two recessed parts 517 are famed on the front side of the upper surface of reagent container holder body 51. These recessed parts 517 are provided with holes for screwing down leaf springs 519 illustrated in FIGS. 11A and 11B.

As illustrated in FIGS. 11A and 11B, each leaf spring 519 is bent outward at the lower end. The lower ends of leaf springs 519 are placed at the positions of respective openings 516 of reagent container holder body 51. Leaf springs 519 make it possible to hold several types of reagent containers 40 with different diameters. When reagent container 40 with a large diameter is mounted on reagent container holder body 51, leaf springs 519 bow outward and the end portions of leaf springs 519 enter openings 516. In this case, reagent container 40 is placed at a predeteimined position in reagent container holder body 51 with the outer circumference of reagent container 40 pressed with the resilience of leaf springs 519. When reagent container 40 with a small diameter is mounted on reagent container holder body 51, leaf springs 519 slightly contact the outer circumference of reagent container 40. Thus, reagent container 40 is placed at a predetermined position in reagent container holder body 51 with a movement of reagent container 40 restricted by leaf springs 519.

Figure 12:
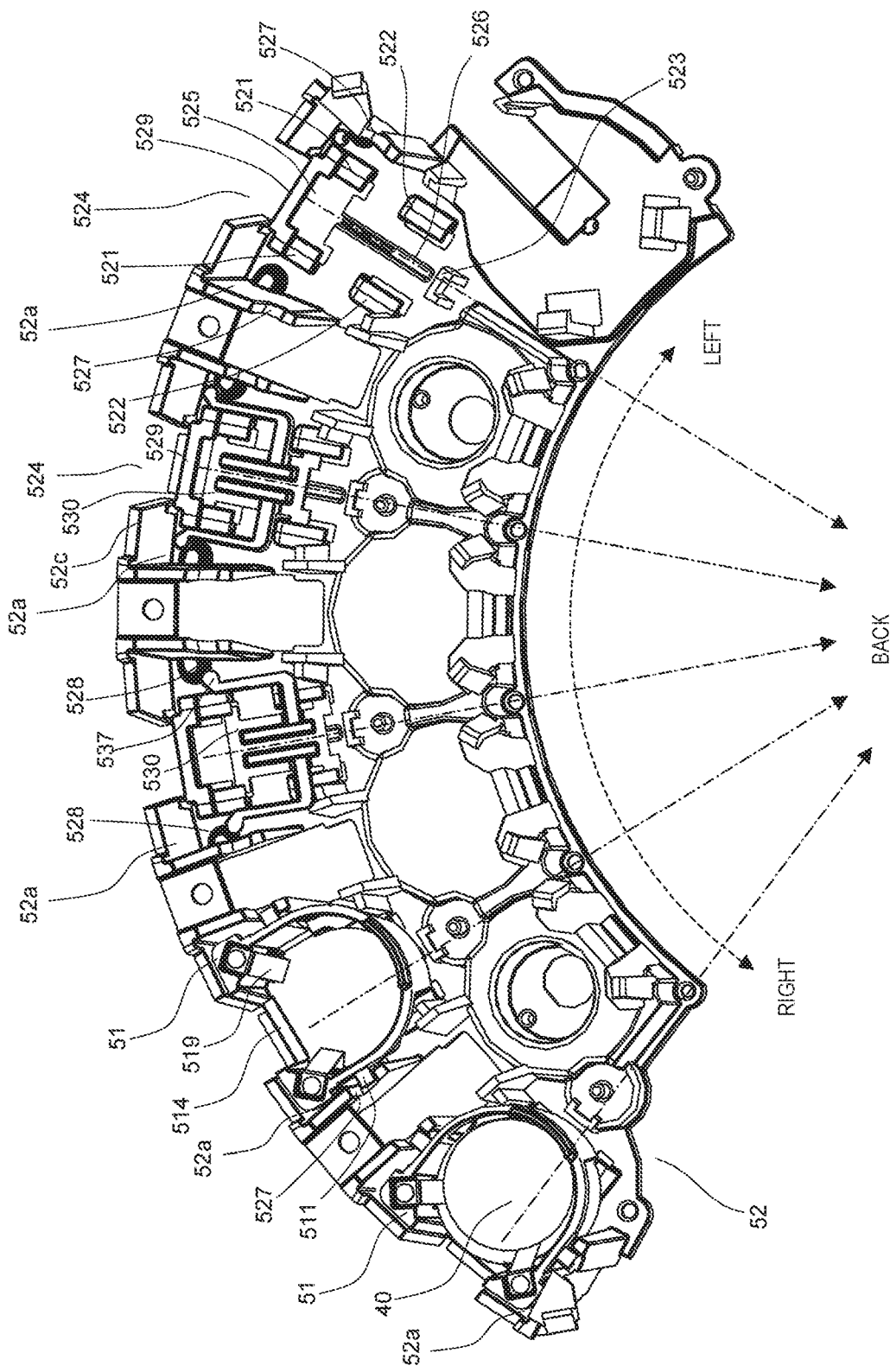
FIG. 12 is a perspective view, viewed from the upper back side, of a support body on which levers, reagent container holder bodies, and a reagent container are mounted in an embodiment.
Figure 13:
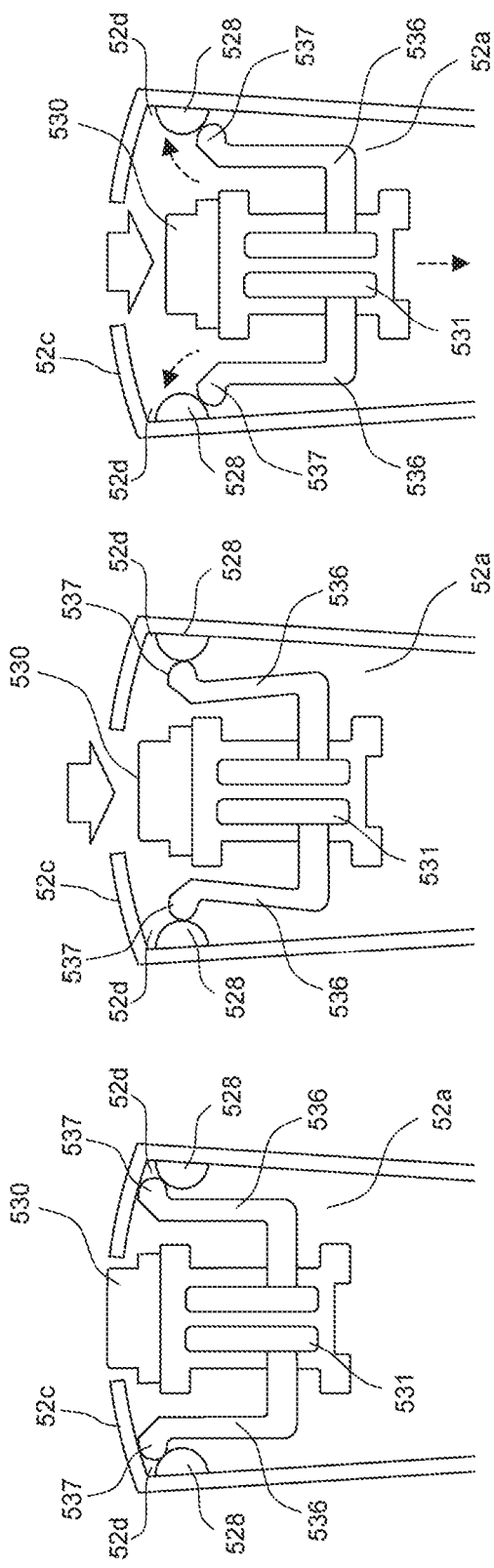
FIGS. 13A to 13C are schematic views illustrating an operation of a tilt changing part along with pushing-in of the lever according to an embodiment.

As illustrated in FIG. 12, lever 530 and reagent container holder body 51 having the aforementioned configurations are installed in each installation area 52a of support body 52. In FIG. 12, a dashed-dotted line arrow is additionally drawn to indicate the back direction of each installation area 52a and a broken-line arrow is additionally drawn to indicate the left direction and the right direction.

In FIG. 12, no component is installed in installation area 52a at the left end, and levers 530 are installed in second and third installation areas 52a from the left. Then, reagent container holder body 51 is installed in fourth installation area 52a from the left. In installation area 52a at the right end, reagent container holder body 51 is installed and reagent container 40 is further held in reagent container holder body 51.

Lever 530 is installed in installation area 52a in such a way that flange parts 533, 534 are fit into guide parts 521, 522 from the back side with operation part 532 inserted in hole 525. Third installation area 52a from the left is illustrated in a state immediately after flange parts 533, 534 are fit into guide parts 521, 522 from the back side. In this state, flange parts 533, 534 and guide parts 521, 522 engage with each other, and projection part 538 on the lower surface of lever 530 gets caught in groove 526 in installation area 52a. Thus, lever 530 is supported to be movable relative to support body 52 in the front-back direction.

From this state, lever 530 is moved to the front side. With this operation, tip end parts 537 of lever 530 get over bumps 528 while being pressed and elastically displaced inward by bumps 528. In this way, tip end parts 537 get caught in the clearances between bumps 528 and wall 52c as illustrated in second installation area 52a from the left. Thus, the movement of lever 530 is restricted and lever 530 is placed at the third position.

After lever 530 is installed in the aforementioned way, reagent container holder body 51 is laid over the upper surface of lever 530 as in fourth installation area 52a from the left. Thus, shafts 511 of reagent container holder body 51 get caught in bearings 527 of support body 52 and thereby reagent container holder body 51 is turnably supported by support body 52. In addition, ridge 518 in FIG. 10A gets caught in groove part 535 in FIG. 8A, and engagement parts 531 in FIG. 8A are sandwiched between protrusions 512, 513 in FIG. 10A.

After completion of installation of levers 530 and reagent container holder bodies 51 in all installation areas 52a, cover 53 is laid on the upper surface of support body 52 as illustrated in FIG. 5. Thus, the upper surfaces of shafts 511 of reagent container holder bodies 51 are pressed by cover 53, and thereby shafts 511 are kept from slipping off. Moreover, handle 54 and seat 55 are attached to support body 52, and thus reagent container holder 50 illustrated in FIGS. 4 and 5 is assembled.

In Embodiment 1, reagent container holder body 51 is turnably supported by the support unit including shafts 511 of reagent container holder body 51 and bearings 527 of support body 52. Here, the support unit only has to support reagent container holder body 51 in a turnable manner, and may include shafts 511, bearings 527, and support members provided between shafts 511 and bearings 527, for example.

With reference to FIGS. 13A to 13C, description is provided for a tilt change operation of reagent container holder body 51. The upper side of each of FIGS. 13A to 13C illustrates a state of lever 530, and the lower side of each of FIGS. 13A to 13C illustrates a state of reagent container holder body 51 with lever 530 put in the state of the upper side.

As illustrated in FIG. 13A, when lever 530 is located at the third position, reagent container holder body 51 takes the upright posture and is placed at the first position. In this state, right and left tip end parts 537 of lever 530 get caught in respective clearance parts 52d which are the clearances between bumps 528 and wall 52c in installation area 52a. Thus, a movement of lever 530 in the front-back direction is restricted. In addition, engagement parts 531 of lever 530 are sandwiched between protrusions 512, 513 on the lower surface of reagent container holder body 51. Thus, the turning of reagent container holder body 51 is restricted, and reagent container holder body 51 is kept in the upright posture.

The user sets reagent container 40 in reagent container holder body 51 in the state of FIG. 13A, and then pushes lever 530 in. Bumps 528 are arranged on the movement routes of tip end parts 537. Each bump 528 juts in a direction in which tip end part 537 can be elastically displaced. For this reason, when the user pushes lever 530 in, right and left aim parts 536 of lever 530 bow inward, or specifically toward engagement parts 531, and tip end parts 537 at the tip ends of aim parts 536 get on bumps 528. Along with this, protrusion 512 is pushed by engagement parts 531 and reagent container holder body 51 turns around shafts 511 in the clockwise direction in the drawing.

When the user further pushes lever 530 in, tip end parts 537 at the tip ends of aim parts 536 get over bumps 528 as illustrated in FIG. 13C. In this case, with the resilience of aim parts 536, backward momentum is generated in lever 530. With the movement of lever 530 toward the back side, protrusion 512 is further pushed by engagement parts 531 and reagent container holder body 51 turns around shafts 511 in the clockwise direction in the drawing. When lever 530 is moved to the fourth position illustrated in FIG. 13C, protrusion 512 hits wall part 523, and the turning of reagent container holder body 51 is restricted. In this state, tip end parts 537 engage with back portions of bumps 528, which restricts a movement of lever 530 toward the front side. Thus, reagent container holder body 51 is kept in the state tilted at a predetermined angle. The movement range of lever 530 is a range between the third position illustrated in FIG. 13A and the fourth position illustrated in FIG. 13C.

In the case of returning reagent container holder body 51 from the state in FIG. 13C to the first position corresponding to the upright posture, the user puts the fingers on operation part 532 of lever 530 and pulls out lever 530 toward the front side. With this operation, lever 530 is returned to the state in FIG. 13A via the state in FIG. 13B. In this case, engagement parts 531 of lever 530 push protrusion 513 of reagent container holder body 51, and reagent container holder body 51 turns in the anticlockwise direction in the drawing. In the case of pulling out lever 530, frontward momentum is generated in lever 530 with the resilience of arm parts 536 after tip end parts 537 get over bumps 528. This allows lever 530 to smoothly return to the state in FIG. 13A. Thus, reagent container holder body 51 is returned to the upright posture.

Since tip end parts 537 of lever 530 get caught in clearance parts 52d or engage with the back portions of bumps 528, the movement of lever 530 is restricted and lever 530 is locked at the third position in FIG. 13A and the fourth position in FIG. 13C. Thus, the posture of reagent container holder body 51 changes over between two stages, which are the upright posture and the posture tilted at the predetermined angle from the upright posture. In other words, aim parts 536, tip end parts 537, and bumps 528 constitute the lock part that locks lever 530 at the third position and the fourth position, and changes the tilt of reagent container holder body 51 between the stages.

In the case where the user moves lever 530 toward the front side or the back side, the movement of lever 530 is promoted with the resilience of aim parts 536 if tip end parts 537 contact portions of bumps 528 other than their peak points. In other words, when lever 530 is located at any position other than the third position illustrated in FIG. 13A and located at any position other than the fourth position illustrated in FIG. 13C, the movement of lever 530 to the third position or the fourth position is promoted. Thus, arm parts 536, tip end parts 537, and bumps 528 constitute a movement promoting unit that promotes a movement of lever 530 at any position other than the two positions illustrated in FIGS. 13A and 13C.

As described with reference to FIGS. 13A to 13C, in Embodiment 1, the simple operation of pushing in lever 530 to the back side or pulling out lever 530 to the front side allows reagent container holder body 51 to be placed at either of two stages, that is, the first position corresponding to the upright posture and the second position corresponding to the posture tilted at the predetermined angle.

Moreover, the movement of lever 530 is promoted by the action of arm parts 536, tip end parts 537, and bumps 528 as described above. This inhibits reagent container holder body 51 from being stopped at a position other than the predetermined tilt position. Thus, reagent container 40 can be set at a desired angle smoothly by such simple operation.

Additionally, since the outside surface of each tip end part 537 is a surface curved in an arc shape and each bump 528 also has a surface curved in an arc shape, tip end parts 537 can smoothly get over bumps 528 with a movement of lever 530. Thus, the user can push in and pull out lever 530 with smooth operation feeling.

In Embodiment 1, since reagent container holder body 51 is supported by shafts 511, the support unit for supporting reagent container holder body 51 in the turnable manner can be formed with the simple configuration. In addition, force applied to lever 530 is transmitted to reagent container holder body 51 via the engagement of engagement parts 531 with any of protrusions 512, 513. Such a simple configuration can be employed to constitute an engagement unit that moves with a movement of lever 530 and engages with reagent container holder body 51.

Figure 14:
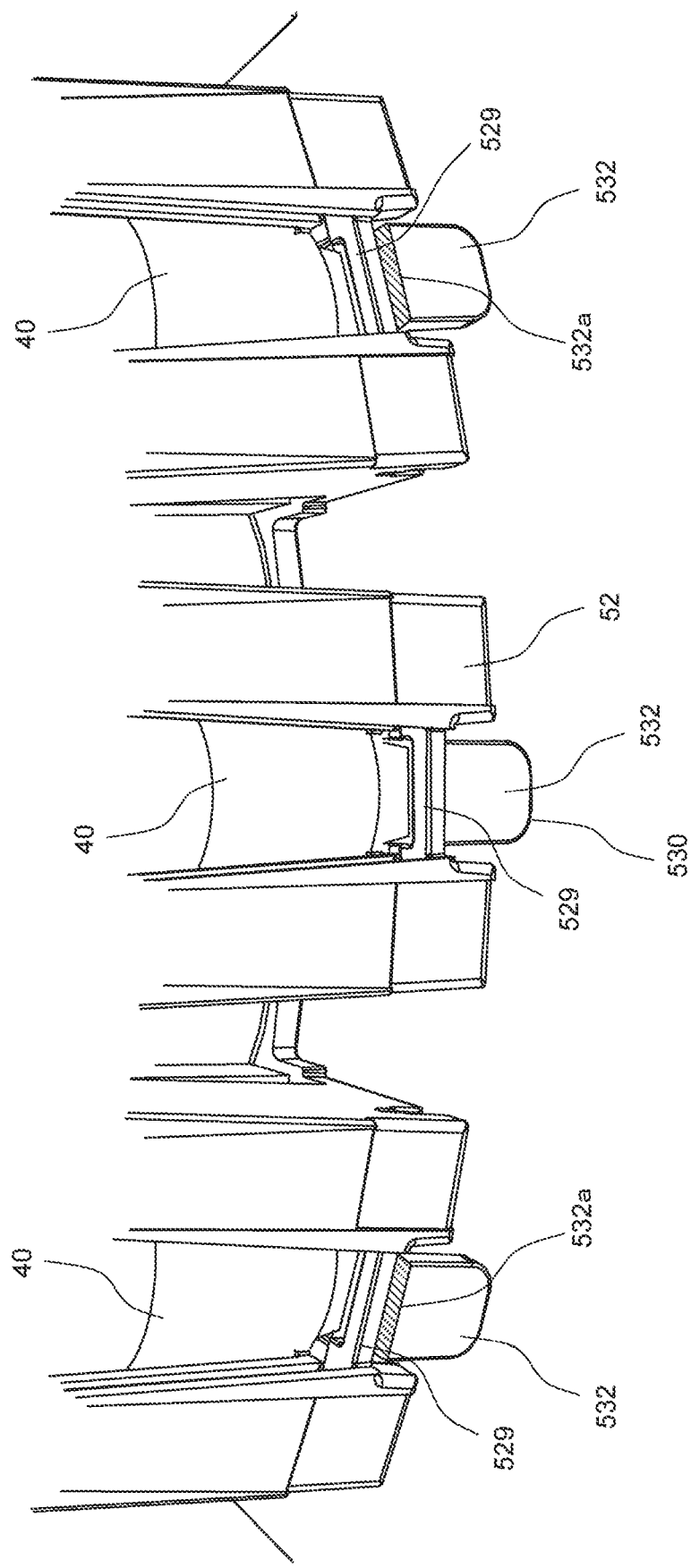
FIG. 14 is a perspective view of part of the front side of the reagent container holder according to an embodiment viewed from above.

As illustrated in FIG. 14, when lever 530 is pushed in, mark area 532a in the upper surface of operation part 532 of lever 530 is hidden by bridge part 529. In FIG. 14, center lever 530 is pushed in backward and placed at the fourth position, and other levers 530 are pulled out frontward and placed at the third positions. For this reason, only mark area 532a in the upper surface of center operation part 532 is hidden by bridge part 529, whereas mark areas 532a on the upper surfaces of other operation parts 532 are exposed.

As described above, mark area 532a is provided with a mark by a process such as coloring, and thereby the visibility of mark area 532a is enhanced. Thus, the user can easily and certainly check whether or not lever 530 is pushed in and placed at the fourth position, by viewing the surroundings of operation part 532. This smoothly prevents a mistake of not operating lever 530 or an inappropriate operation on lever 530.

Figure 15A:
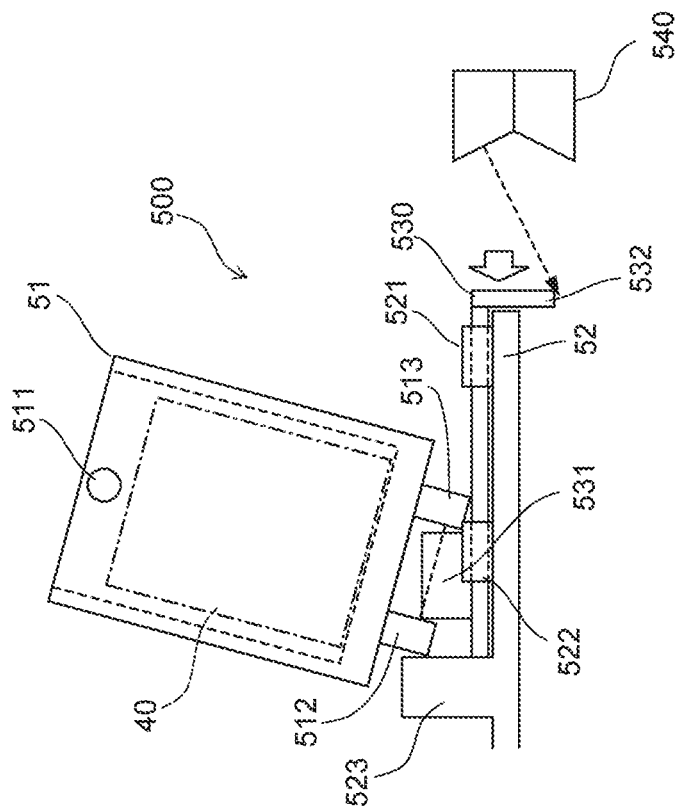
FIGS. 15A and 15B are schematic side views illustrating a configuration for detecting a tilt of a reagent container according to an embodiment.
Figure 15B:
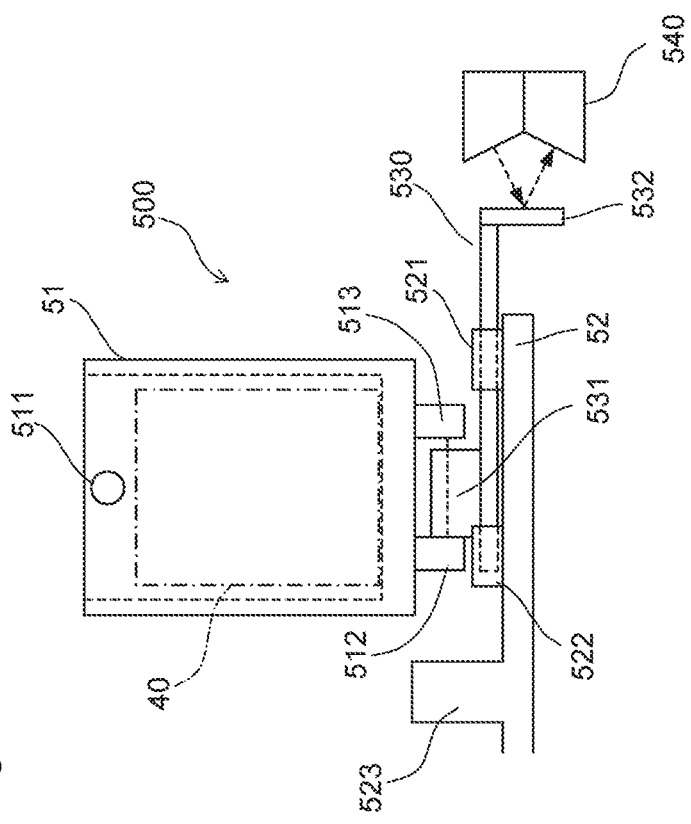

As illustrated in FIGS. 15A and 15B, measurement unit 100 in FIG. 1A includes tilt detector 540 arranged around the outer circumference of reagent table 120. Tilt detector 540 is arranged, for example, at the same circumferential position as barcode reader 140. In the configuration example in FIGS. 15A and 15B, tilt detector 540 includes a photocoupler. Tilt detector 540 may include any other detection member.

As illustrated in FIG. 15A, when lever 530 is located at the third position, light emitted from a light emitter of the photocoupler is reflected by the front surface of operation part 532, and is then received by a light receiver of the photocoupler. As illustrated in FIG. 15B, when lever 530 is located at the fourth position, light emitted from the light emitter of the photocoupler is not received by the light receiver of the photocoupler. Whether lever 530 is located at the third position or the fourth position can be detected depending on whether the light receiver of the photocoupler receives light or not. Tilt detector 540 outputs a detection signal depending on a light reception state of the light receiver.

As illustrated in FIG. 16A, sample analyzer 10 includes measurement unit 100, transport unit 200, and information processing unit 300. Measurement unit 100 includes measurement unit 101, sensor 102, driver 103, communication unit 104, controller 105, and storage 106.

Measurement unit 101 includes detection unit 170 and heater table 150 illustrated in FIG. 1A, and so forth. Sensor 102 includes barcode readers 140, 210, tilt detector 540 illustrated in FIGS. 15A and 15B, and other sensors. Driver 103 includes a drive motor that drives sample dispenser 110 illustrated in FIG. 1A, drive motors that drive aspiration tubes 165, 166 of reagent dispensers 161, 162, an air pressure source, and others. Communication unit 104 performs communication with information processing unit 300. Controller 105 includes an arithmetic processing circuit such as a CPU, and controls the components in accordance with a program stored in storage 106. Storage 106 includes a storage medium such as a ROM, a RAM, or a hard disk.

Information processing unit 300 includes controller 301, output unit 302, and input unit 303. Information processing unit 300 is formed of, for example, a personal computer. Controller 301 includes an arithmetic processing circuit such as a CPU, and a storage medium such as a ROM, a RAM, or a hard disk. Output unit 302 includes a monitor, a speaker, and so on. Input unit 303 includes input devices such as a keyboard, a mouth, and a touch panel. Controller 301 analyzes as described above the measurement results received from the measurement unit 100, that is, signals outputted from photosensor 171c illustrated in FIGS. 2A and 2B, and displays the analysis result on output unit 302. Then, information processing unit 300 outputs, via output unit 302, information based on the signals received from measurement unit 100

Storage 106 in measurement unit 100 retains a table illustrated in FIG. 16B. In the table, a container ID that identifies a type of reagent container 40 and a tilt position of reagent container 40 are associated with each other. The tilt position "1" is the position in the upright posture, and the tilt position "2" is the position in the posture tilted just at the predetermined angle from the upright posture. The tilt positions are set in advance by a service person, for example, on the basis of the heights and diameters of reagent containers 40. In the case where reagent container holder 50 is newly set on reagent table 120 in order to replace reagents or do the like, controller 105 judges whether the tilt state of each reagent container 40 is appropriate or not by referring to the table in FIG. 16B.

Figure 17B:
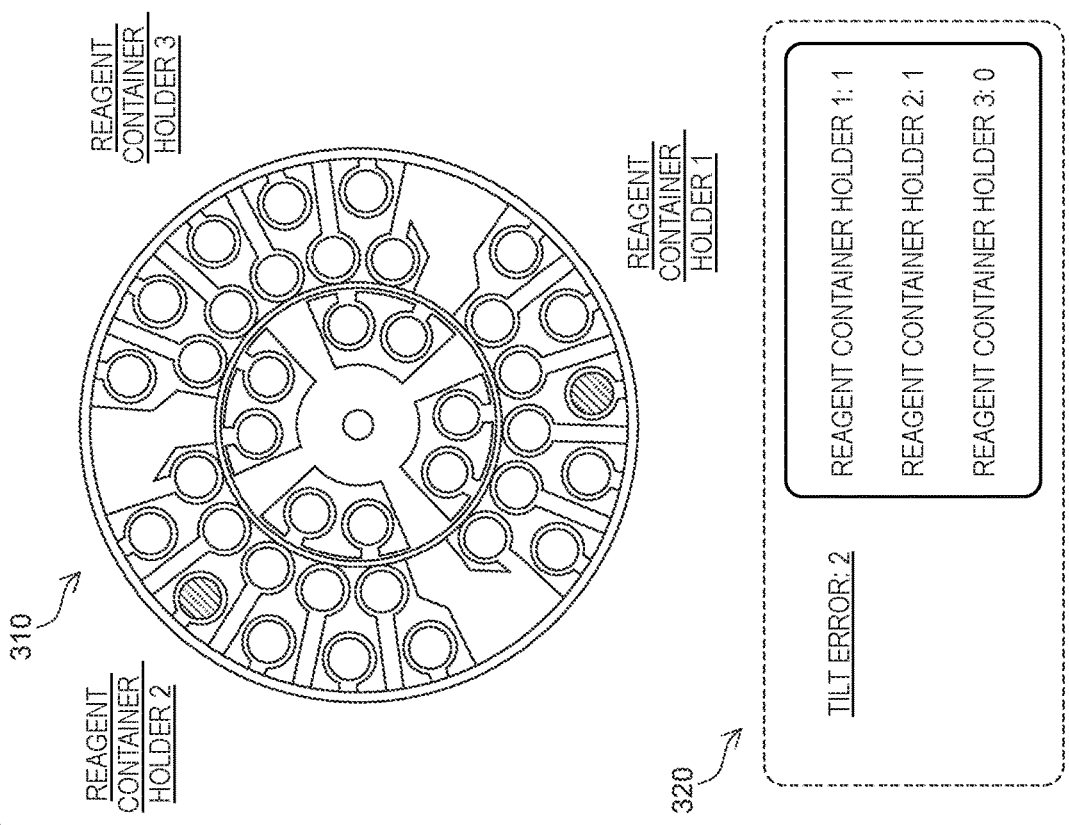
FIG. 17B is a view illustrating a display example of a screen on which a result of appropriateness judgments of tilts of reagent containers is outputted according to an embodiment.
Figure 17A:
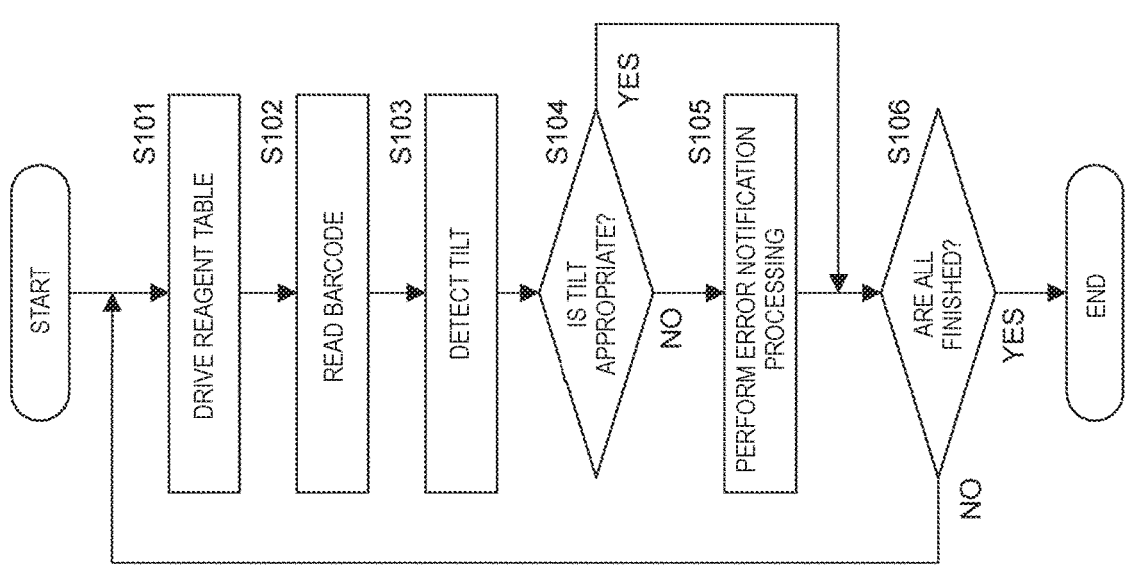
FIG. 17A is a processing flowchart of appropriateness judgments of tilts of reagent containers according to an embodiment.

According to a flowchart presented in FIG. 17A, controller 105 makes tilt judgments of reagent containers 40.

In step S101, controller 105 drives reagent table 120 and places one of reagent containers 40 set in reagent container holder 50 at a reading position of barcode reader 140. In step S102, controller 105 causes barcode reader 140 to read the barcode of reagent container 40 placed at the reading position. In step S103, controller 105 also detects the tilt position of reagent container 40 on the basis of the detection signal from tilt detector 540. In step S104, controller 105 fetches, from the table in FIG. 16B retained in the storage 106, the tilt position associated with the container ID of reagent container 40 obtained by the barcode reading, and compares the fetched tilt position with the tilt position detected from the detection signal of tilt detector 540.

If a judgment result in step S104 is No, that is, if the tilt position fetched from the table does not match the tilt position detected from the detection signal, controller 105 perfoims error notification processing for concerned reagent container 40 in step S105. If the judgment result in step S104 is YES, that is, if the tilt position fetched from the table matches the tilt position detected from the detection signal, controller 105 skips step S105 and advances the processing to step S106.

In step S106, controller 105 judges whether the tilt judgments on all reagent containers 40 regarded as judgment targets are completed or not. If a judgment result in step S106 is No, that is, if the tilt judgments on all reagent containers 40 are not completed, controller 105 returns the processing to step S101, and performs the same processing for next reagent container 40. In this way, controller 105 makes the tilt judgments on all reagent containers 40 regarded as the judgment targets.

In step S105, controller 105 sends information processing unit 300 the set position of reagent container 40 from which a tilt error is detected and the type of reagent container 40. Upon receipt of this, controller 301 of information processing unit 300 causes output unit 302 to display a screen for notifying the user of the tilt error. For example, controller 301 causes output unit 302 to display a screen illustrated in FIG. 17B.

The screen of FIG. 17B includes layout image 310 presenting a layout of reagent containers in reagent table 120, and tilt error detection result 320. In layout image 310, texts identifying three reagent container holders 50 are provided in addition, and the set positions of reagent containers from which tilt errors are detected are colored in a predetermined color. In FIG. 17B, the set positions of reagent containers 40 from which the tilt errors are detected are hatched by oblique lines. The detection result 320 presents the total number of tilt errors detected, and the number of tilt errors in each reagent container holder 50. In summary, the screen of FIG. 17B provides the information on the appropriateness of the tilts of reagent container holder bodies 51, by coloring the set position from which each tilt error is detected in layout image 310, and by presenting the total number of tilt errors detected, and the number of tilt errors in each reagent container holder 50 in detection result 320.

Referring to the screen illustrated in FIG. 17B, the user can recognize the reagent container 40 to tilt inappropriately, and take a measure to correct the tilt. The tilt error notification screen is not limited to the structure illustrated in FIG. 17B, but may employ any other structure. In addition, the tilt error notification method is not limited to a notification on a screen, but may be any other methods such as voice messages or indicator display.

If a tilt error of reagent container 40 is detected, controller 105 suspends the measurement of samples. This is because, if the measurement is perfoiined with a high height and small diameter reagent container 40 tilted by mistake as illustrated in FIG. 3C, aspiration tube 165, 166 may cause a damage or the like by hitting the upper surface of reagent container 40. Controller 105 suspends the measurement until the tilts of all reagent containers 40 become appropriate. After the user corrects the tilts of all reagent containers 40 from which the tilt errors are detected, controller 105 starts the measurement operations on the samples.

Incidentally, in the case of low height and large diameter reagent container 40 illustrated in FIGS. 3A and 3B, aspiration tube 165, 166 does not hit the upper surface of reagent container 40 regardless of whether reagent container 40 is tilted or not. For this reason, even if such reagent container 40 is set in the upright posture and a tilt error is detected therefrom, the measurement operation itself does not have any trouble. Accordingly, against such an error, the measurement operation may be continued forward while making the error notification. In the screen of FIG. 17B, a tilt error which disables the measurement operation from proceeding, and a tilt error which allows the measurement operation to proceed may be displayed distinctively by a method such as one displaying the errors with different colors in layout image 310.

As illustrated in FIGS. 13A to 13C, tip end parts 537 are elastically displaced with arm parts 536 bent. In another possible configuration, bumps 528 may be elastically displaced outward.

Moreover, the shape of bump 528 in plan view is not limited to the arc shape illustrated in FIG. 7, but may be any other shape such as an equilateral triangle, an isosceles triangle, a right triangle, and a mountain-like shape asymmetric in the movement direction of lever 530. The shape of tip end part 537 in plan view is not limited to the arc shape illustrated in FIGS. 8A and 8B, but may be any other shape such as a triangle, an ellipse, and a trapezoid.

Embodiment 2

In Embodiment 2, tilts of reagent container holder bodies 51 are automatically controlled on the basis of detection signals from tilt detector 540.

Figure 18A:
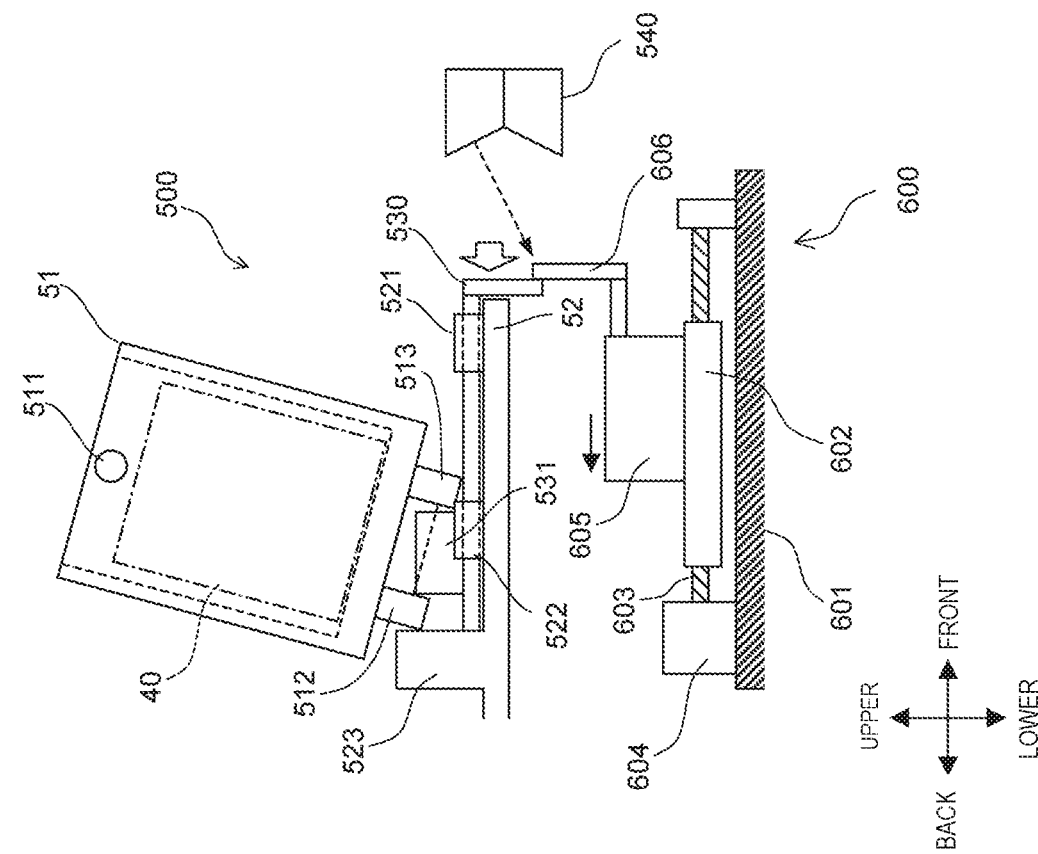
FIGS. 18A and 18B are schematic side views each illustrating a configuration and an operation of a driver that drives a tilt changing part in an embodiment.
Figure 18B:
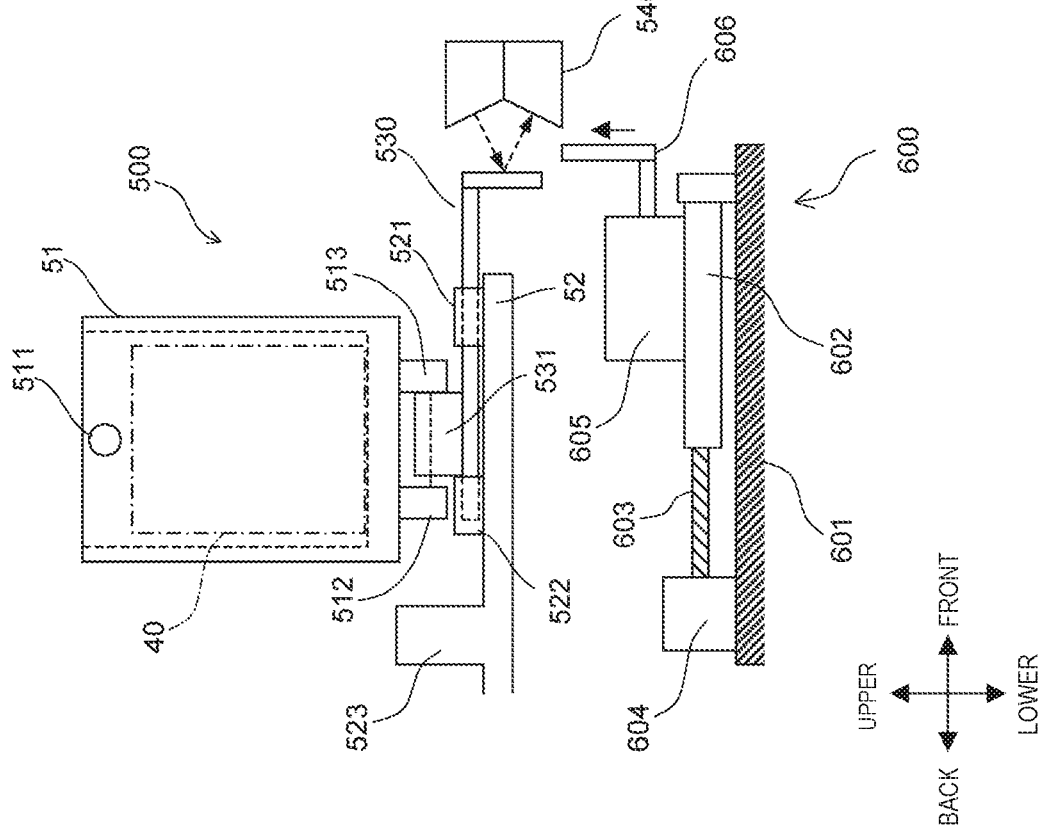

As illustrated in FIGS. 18A and 18B, measurement unit 100 is provided with drive mechanism 600 for driving tilt changing part 500. Drive mechanism 600 moves lever 530 in a direction of pushing in lever 530 backward, and in a direction of pulling out lever 530 frontward.

Drive mechanism 600 includes base 601, movement part 602, gear 603, motor 604, lift 605, and lever 606. Movement part 602 is supported on base 601 so as to be movable in front-back directions. A driving force of motor 604 is transmitted to movement part 602 through gear 603. Lift 605 is arranged on movement part 602, and includes a lift mechanism that lifts up and down lever 606. The lift mechanism includes, for example, a mechanism part including a jack, a cam, and so forth, and a driving source such as a drive motor.

In the case where reagent container 40 with a low height and large diameter is set in reagent container holder body 51 as illustrated in FIG. 18A, reagent container holder body 51 needs to be placed at the second position where reagent container holder body 51 is tilted. In this case, drive mechanism 600 places movement part 602 at a foremost position with lever 606 placed at a lowest position. In this state, drive mechanism 600 lifts up lever 606 to a highest position, and then moves movement part 602 backward by a predetermined distance. With this operation, lever 530 is pushed in backward and placed at the fourth position, and reagent container holder body 51 is placed at the second position, as illustrated in FIG. 18B.

In the case where reagent container 40 with a high height and small diameter is set in reagent container holder body 51 as illustrated in FIG. 19A, reagent container holder body 51 needs to be placed at the first position where reagent container holder body 51 takes the upright posture. In this case, drive mechanism 600 places movement part 602 at a back-end position with lever 606 placed at the lowest position. In this state, drive mechanism 600 lifts up lever 606 to the highest position, and then moves movement part 602 frontward by a predetermined distance. With this operation, lever 530 is pulled out frontward and placed at the third position, and reagent container holder body 51 is placed at the first position, as illustrated in FIG. 19B.

Figure 20B:
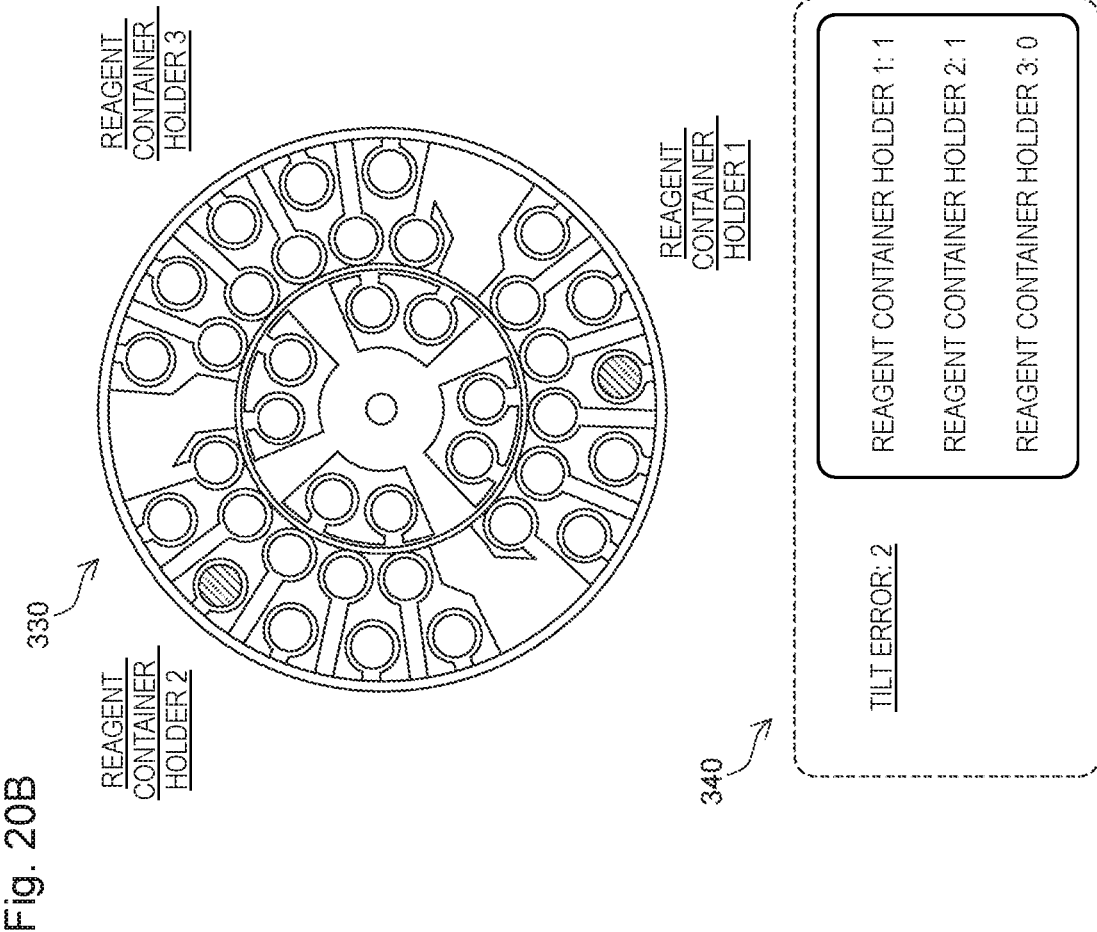
FIG. 20B is a view illustrating a display example of a screen on which a correction result of tilt correction control of reagent containers is outputted according to an embodiment.
Figure 20A:
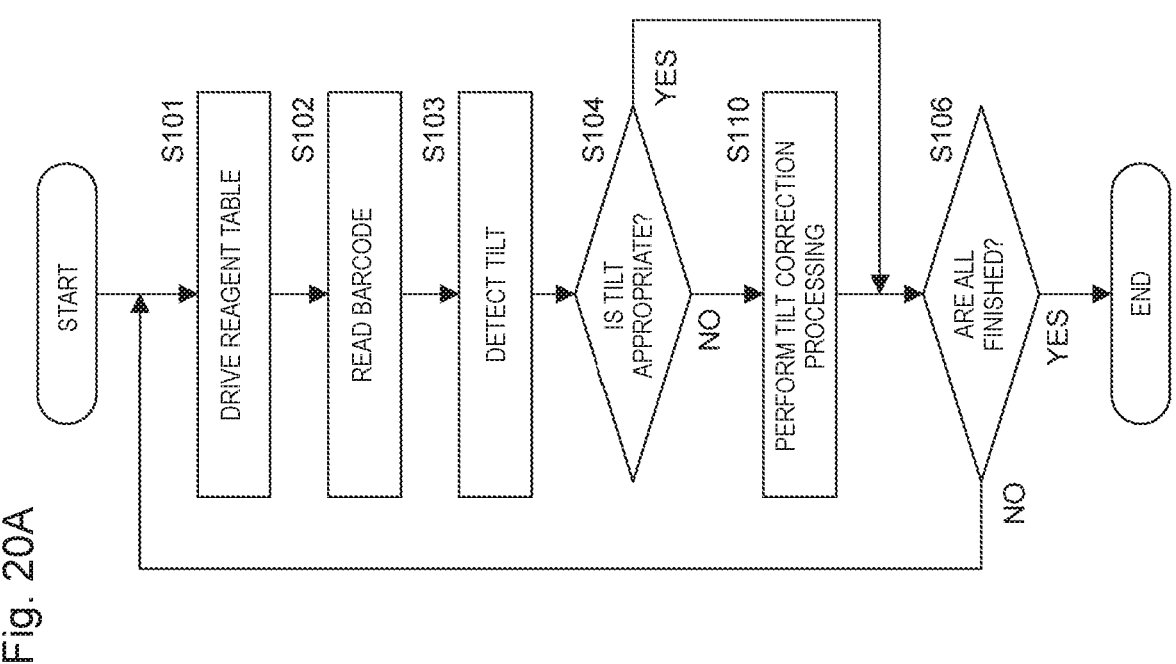
FIG. 20A is a processing flowchart of tilt correction control of reagent containers according to an embodiment.

In accordance with a flowchart presented in FIG. 20A, controller 105 corrects tilts of reagent containers 40. In the flowchart of FIG. 20A, step S105 in the flowchart of FIG. 17A is replaced with step S110. The other steps in the flowchart of FIG. 20A are the same as those in FIG. 17A.

If a judgment result in step S104 is No, that is, if the tilt of reagent container holder body 51 is inappropriate, controller 105 perfoiins tilt correction processing for reagent container holder body 51 in step S110. The tilt correction processing is perfoimed in the way already described with reference to FIGS. 18A, 18B, 19A and 19B. Controller 105 preforms the tilt correction processing for all reagent containers 40 regarded as targets.

When measurement unit 100 automatically corrects the tilts of reagent containers 40 in the aforementioned way, measurement unit 100 can smoothly shift to the measurement of the samples. In Embodiment 1 described above, in response to a tilt error notification, the user has to take out reagent container holders 50 from reagent table 120 once, operate levers 530, and thereafter set reagent container holders 50 in reagent table 120 again. In Embodiment 2, such operation is unnecessary, and the tilts of reagent containers 40 are automatically corrected. This enables a reduction in the time and labor of the user, and a smooth shift to the sample measurement.

Incidentally, in step S110, in addition to execution of the tilt correction processing, controller 105 may also send information processing unit 300 the set position of reagent container 40 for which the tilt correction is performed, and the container ID of concerned reagent container 40. In this case, information processing unit 300 causes output unit 302 to display a screen illustrated in FIG. 20B as is the case with the error notification. In this screen, the set positions of reagent containers 40 for which the tilt corrections are performed are displayed by being colored, for example, in layout image 330, and the total number of reagent containers 40 for which the tilt corrections are performed and the number of tilt corrections in each reagent container holder 50 are displayed in a region of detection result 340. From this screen, the user can know the presence of reagent containers 40 for which the tilt corrections are performed.

Embodiment 3

In Embodiment 3, tilt changing part 500 includes lever 580, engagement part 582, guide part 572, a support unit, a lock part, and a cam part. In Embodiment 3, the cam part to be described later is added to tilt changing part 500 in Embodiments 1, 2, and lever 580, engagement part 582, guide part 572, the support unit, and the lock part are different from those in Embodiments 1, 2. In Embodiment 3, engagement part 582 is famed on lever 580, and guide part 572 is famed on support body 57.

Lever 580 and engagement part 582 change a tilt of reagent container holder body 56. Guide part 572 allows lever 580 to smoothly move among a third position and fourth positions to be described later. The support unit supports reagent container holder body 56 in a turnable manner. The lock part locks lever 580 at the third position and the fourth positions to be described later. The cam part converts a turn movement of lever 580 in the horizontal direction to a turn movement of reagent container holder body 56 in a direction intersecting the horizontal direction. The support unit and the lock part in Embodiment 3 are described later in detail.

Support body 57 includes a pair of flange parts 571 curved in arc shapes. Reagent container holder body 56 includes a pair of guide grooves 561 having arc shapes and engaging with the pair of flange parts 571, respectively. When flange parts 571 and guide grooves 561 are engaged with each other, reagent container holder body 56 is tiltably supported by support body 57. In other words, reagent container holder body 56 is tiltably supported by the support unit constituted by flange parts 571 and guide grooves 561. Note that the support unit just has to be capable of supporting reagent container holder body 56 in a tiltable manner, and may include, for example, flange parts 571, guide grooves 561, and support members provided between flange parts 571 and guide grooves 561.

Reagent container holder body 56 is famed of a frame-shaped member as in reagent container holder body 51 in Embodiment 1. Opening 562 for reading the barcode of reagent container 40 is formed in the front side of reagent container holder body 56.

Figure 22B:
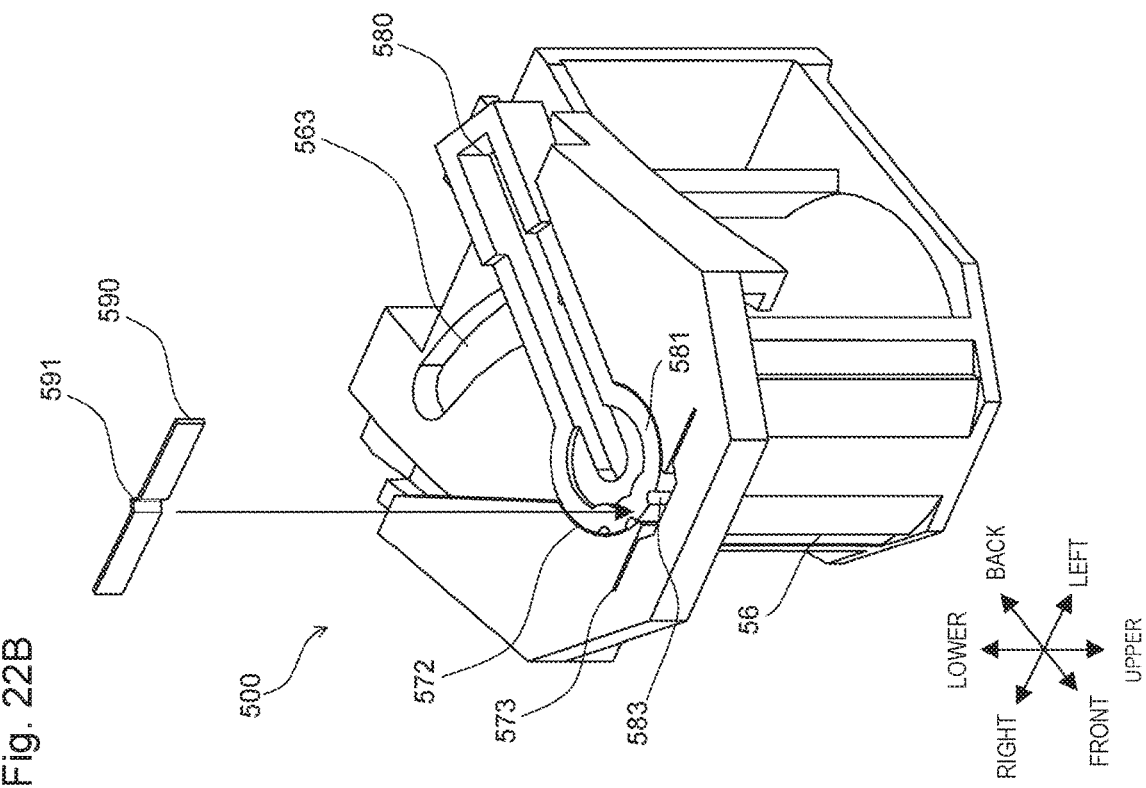
FIG. 22B is a perspective view of the tilt changing part according to an embodiment viewed from the lower back side.
Figure 22A:
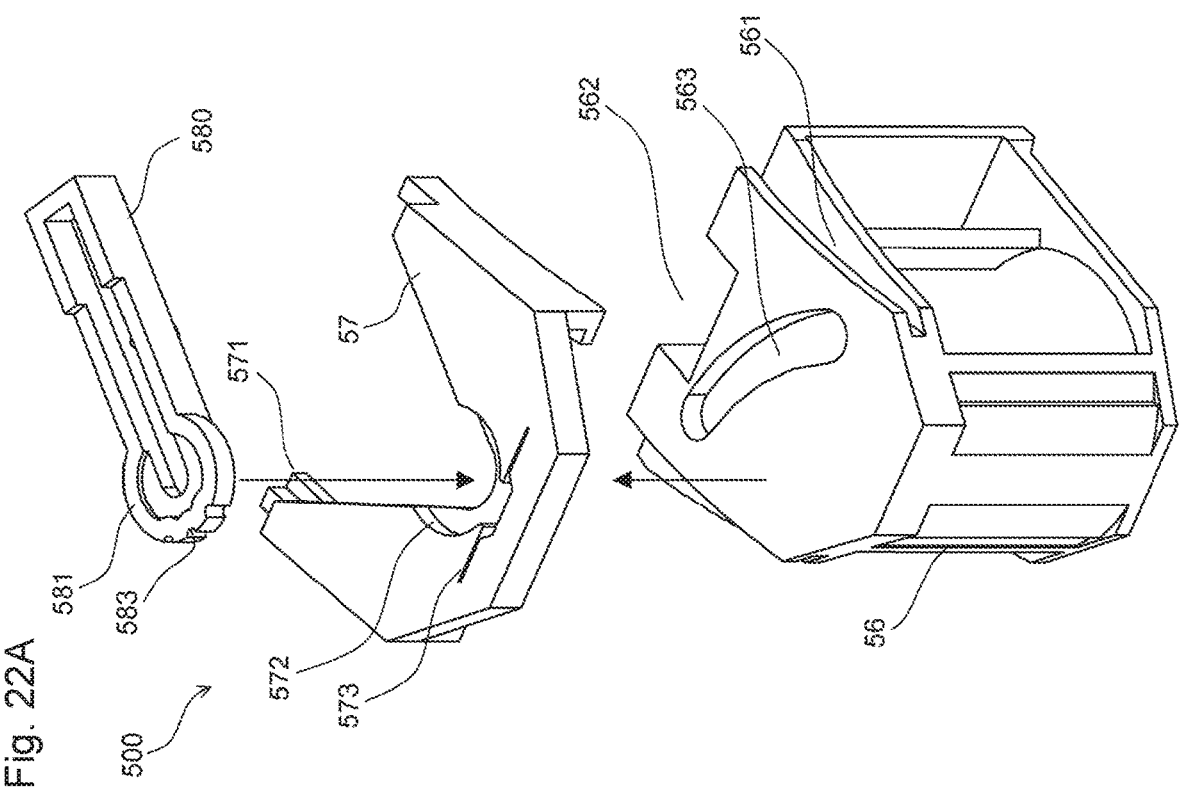
FIG. 22A is a perspective exploded view of the tilt changing part according to an embodiment viewed from the lower back side.

As illustrated in FIG. 22A, an end portion of lever 580 is famed to be arc part 581 in a circular shape in plan view. Three dents 583 are formed on an outer circumferential surface of arc part 581. Guide part 572 being an arc-shaped recessed part into which arc part 581 is to be fit is famed on the lower surface of support body 57. Slit 573 continuous from guide part 572 is formed in front of guide part 572. As illustrated in FIG. 22B, arc part 581 is fit into guide part 572, and leaf spring 590 is also inserted into slit 573. Projection 591 projecting backward is provided to a central portion of leaf spring 590. In the state where leaf spring 590 is inserted in slit 573, projection 591 of leaf spring 590 is snapped in any of three dents 583 provided to the outer circumference of arc part 581. This restricts turning of lever 580. The turning of lever 580 is restricted at the position where projection 591 of leaf spring 590 is snapped in each of dents 583.

Lever 580 is capable of turning and moving in the horizontal direction. The turn range of lever 580 is a range between turn positions where projection 591 of leaf spring 590 is snapped in both end dents 583 among three dents 583, respectively. Center dent 583 is provided at the central position between both end dents 583.

As illustrated in FIG. 22A, arc-shaped groove part 563 is famed on the lower surface of reagent container holder body 56. In addition, as illustrated in FIG. 21A, engagement part 582 in a spherical shape protruding upward is famed on the upper surface of lever 580. In an assembled state in FIG. 22B, engagement part 582 of lever 580 enters groove part 563 of reagent container holder body 56. Thus, in the assembled state in FIG. 21B, when lever 580 is turned, side surfaces of groove part 563 are pushed by engagement part 582, and a lower portion of reagent container holder body 56 is moved backward. Thereby, reagent container holder body 56 is tilted frontward from the upright posture.

Tilt changing part 500 in Embodiment 3 includes the cam part that converts the turn movement of lever 580 in the horizontal direction to the turn movement of reagent container holder body 56 in the direction intersecting the horizontal direction as described above. In Embodiment 3, the cam part is constituted by guide grooves 561, flange parts 571, groove part 563, and engagement part 582.

Figure 23A:
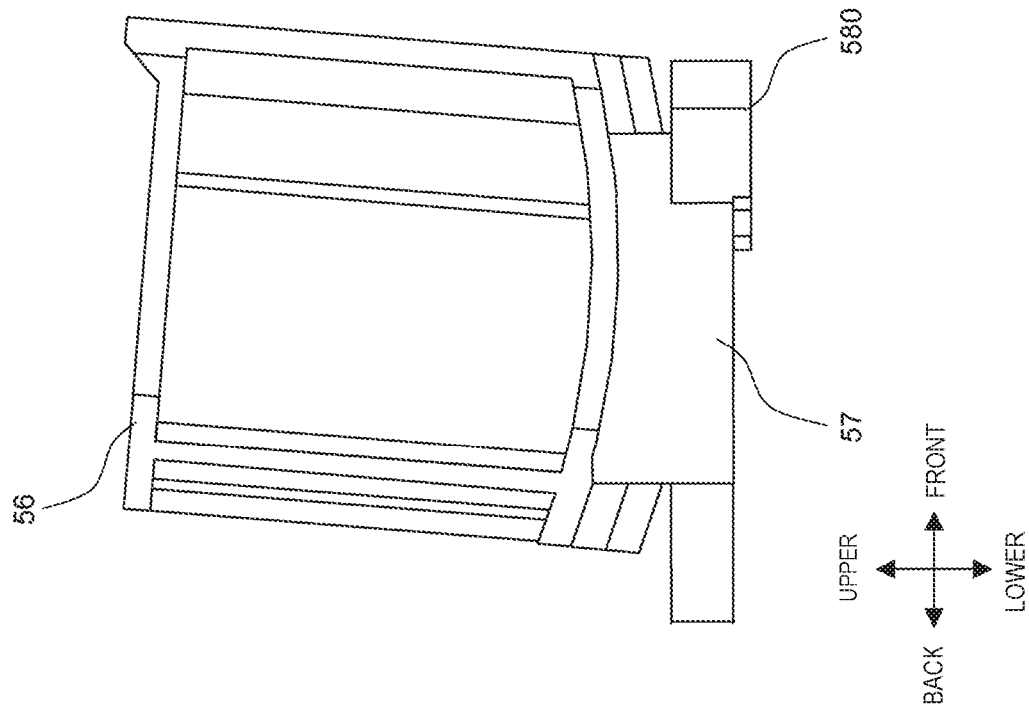
FIGS. 23A and 23B are side views illustrating an operation of the tilt changing part according to an embodiment.

In FIG. 23A, reagent container holder body 56 is placed at the first position corresponding to the upright posture, and lever 580 is placed at the third position. When lever 580 is turned from the state in FIG. 23A, reagent container holder body 56 is tilted frontward. As described with reference to FIG. 22B, lever 580 is restricted to each of the three turn positions by an engagement of projection 591 of leaf spring 590 with the corresponding one of three dents 583 of lever 580. Thus, the user can place lever 580 at each of the three turn positions with an operation feeling of snapping projection 591 into corresponding dent 583. Therefore, the user can place reagent container holder body 56 at the three positions, namely, the first position corresponding to the upright posture, and two tilt positions that are second positions with larger tilts than in the first position.

Figure 23B:
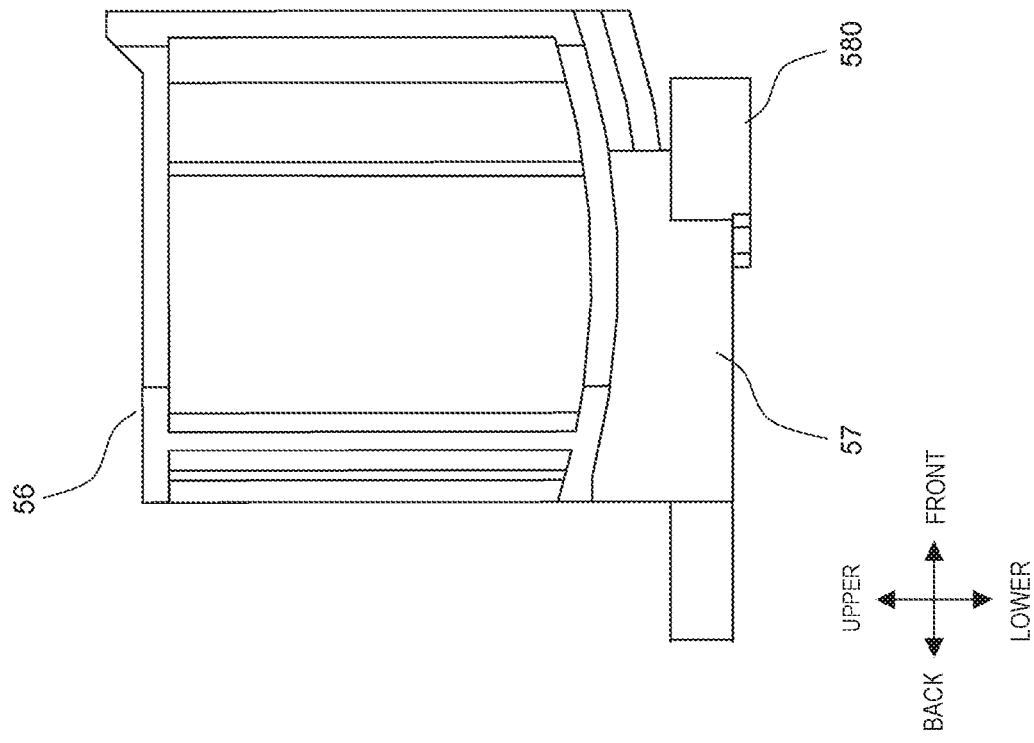

As illustrated in 23A, the position at which reagent container holder body 56 takes the upright posture is the first position. As illustrated in FIG. 23B, the position at which reagent container holder body 56 holds reagent container 40 at a larger tilt than that of reagent container 40 held in reagent container holder body 56 placed at the first position is the second position. As described with reference to FIGS. 21A to 23B, tilt changing part 500 in Embodiment 3 is also configured to move reagent container holder body 56 to the first position and the second positions.

The first position is not limited to the position of reagent container holder body 56 in the upright posture, but may be any position other than the position of reagent container holder body 56 in the upright posture as long as a tilt of reagent container 40 held in reagent container holder body 56 is smaller than in the case of the second position. Similarly, the second positions are not limited to the position of reagent container holder body 56 illustrated in FIG. 23B, but may be any positions other than the position of reagent container holder body 56 illustrated in FIG. 23B as long as a tilt of reagent container 40 held in reagent container holder body 56 is larger than in the case of the first position.

Lever 580 is movable among the third position illustrated in FIG. 22B, and the fourth positions being turn positions different from the position in the state of FIG. 22B. When lever 580 is placed at the third position with engagement part 582 engaging with reagent container holder body 56, reagent container holder body 56 is placed at the first position. When lever 580 is placed at one of the fourth positions with engagement part 582 engaging with reagent container holder body 56, reagent container holder body 56 is placed at the corresponding second position.

Projection 591 of leaf spring 590 and dents 583 of lever 580 constitute the lock part that locks lever 580 at the third position and the fourth positions, and thereby changes the tilt of reagent container holder body 56 stepwise.

In Embodiment 3, engagement part 582 is constituted by a protrusion provided to lever 580, and this protrusion engages with reagent container holder body 56. However, the engagement part is not limited to this, and only has to move with a movement of lever 580 and to engage with reagent container holder body 56. For example, the engagement part may be constituted by a protrusion provided to lever 580, and a member which brings this protrusion into engagement with reagent container holder body 56.

In Embodiment 3, guide part 572 is constituted by the arc-shaped recessed part provided to support body 57, and lever 580 is guided by this recessed part to move among the third position and the fourth positions. However, the guide part is not limited to this, and only has to guide a movement of lever 580 among the third position and the fourth positions. For example, the guide part may be constituted by an arc-shaped recessed part provided to support body 57 and a member provided between this recessed part and lever 580 and configured to guide lever 580.

Operating lever 580, the user places reagent container holder body 56 at a position suitable for reagent container 40 held in reagent container holder body 56. In this way, as in Embodiment 1, almost all the reagent contained in reagent container 40 can be aspirated with aspiration tube 165, 166. This makes it possible to analyze a sample by using reagents contained in various reagent containers while reducing the dead volumes of the reagents.

Also in Embodiment 3, it is preferable to provide measurement unit 100 with a tilt detector that detects a tilt of each reagent container holder body 56 and to notify the user of whether the tilt of reagent container 40 is appropriate or not as in Embodiment 1. In this case, for example, photocouplers are provided at the three turn positions of lever 580, and the tilt position of reagent container holder body 56 can be detected on the basis of the detection signals from the respective photocouplers. This allows the user to correct the tilt of reagent container 40 smoothly.

Moreover, also in Embodiment 3, it is preferable to provide measurement unit 100 with a drive mechanism that drives lever 580, and to automatically correct the tilt of reagent container 40, as in Embodiment 2. Also in this case, it is possible to employ a configuration to turn lever 580 by way of a lever that is lifted up and down and moved horizontally as in Embodiment 2. This enables a reduction in the time and labor of the user to correct the tilt of each reagent container 40, and a smooth shift to the sample measurement operation.

The method of changing the tilt of reagent container holder body 51, 56 stepwise is not necessarily the method involving restricting a movement of lever 530, 580, but may be a method involving restricting a movement of reagent container holder body 51, 56 itself.

Further, the tilt of reagent container holder body 51, 56 is changed between two stages in Embodiment 1 and among three stages in Embodiment 3. Instead, the tilt of reagent container holder body 51 may be changed among three or more stages in the configuration of Embodiment 1, or the tilt of reagent container holder body 56 may be changed between two stages or among four or more stages in Embodiment 3.

Of clinical tests, a blood coagulation test, for example, involves analyzing a sample by using reagents which are sold by various manufacturers and are contained in various types of reagent containers different in height, diameter, and container's bottom shape. The configuration of Patent Literature 1 can hold the reagent containers only at a predetermined angle. For this reason, if various types of reagent containers as described above are used in sample analysis, some types of reagent containers may make it difficult to analyze samples using the reagents contained in the reagent containers while reducing the dead volumes of the reagents.

According to the embodiments described above, it is possible to analyze a sample by using reagents contained in various reagent containers while reducing the dead volumes of the reagents.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

What is claimed is:

1. A sample analyzer comprising:
a controller;
a carousel rotatably supporting a plurality of reagent container holders in a circular arrangement in a horizontal plane about a central axis, each reagent container holder comprising a lever and configured to hold a reagent container at an adjustable tilt with respect to the horizontal plane;
a code scanner configured to read a code attached to the reagent container held by the reagent container holder;
a drive unit configured to adjust the tilt of one of the reagent container holders by moving a position of the lever under control of the controller;
a reagent dispenser configured to aspirate a reagent in the reagent container; and
a detector configured to detect a signal of analyte in a sample which is mixed with the reagent aspirated by the reagent dispenser; wherein
the controller determines an appropriate tilt for each of the plurality of reagent container holders based on a result of reading by the code scanner of the respective code attached to each of the plurality of reagent containers held by the plurality of reagent container holders, and controls the drive unit to adjust the tilt of at least one of the plurality of reagent container holders according to the determined appropriate tilt based on the result of reading the respective code.

2. The sample analyzer according to claim 1, wherein
the lever is capable of being positioned at least at a first position and a second position,
the reagent container held by the reagent container holder stands at a first tilt in a state where the lever is positioned at the first position, and
the reagent container held by the reagent container holder stands at a second tilt, which is greater than the first tilt, in a state where the lever is positioned at the second position.

3. The sample analyzer according to claim 1, wherein the lever is slidably arranged on a guide configured to guide a movement of the lever between a first position and a second position.

4. The sample analyzer according to claim 1, wherein the lever is configured to be locked at a first position and locked at a second position.

5. The sample analyzer according to claim 1, wherein the lever comprises a mark arranged to be exposed when the lever is in a first position and be retracted not to be exposed when the lever is in a second position.

6. The sample analyzer according to claim 1, further comprising:
a tilt detector configured to detect the tilt of the reagent container holder, wherein
the controller identifies one or more reagent containers, on the carousel, with an inappropriate tilt on the basis of the identification of the reagent container and a result of a detection of tilt by the tilt detector.

7. The sample analyzer according to claim 6, wherein the controller refers to a configurable database defining an appropriate tilt for each of reagent IDs stored in a memory, for identifying the one or more reagent containers with an inappropriate tilt.

8. The sample analyzer according to claim 6, wherein the controller generates an alert in response to identifying one or more reagent containers with an inappropriate tilt.

9. The sample analyzer according to claim 6, wherein the controller outputs a screen, on a display, illustrating an arrangement of the reagent containers on the carousel, in which the identified reagent container is shown distinctively.

10. A sample analyzing method in a sample analyzer comprising: a controller; a carousel rotatably supporting a plurality of reagent container holders in a circular arrangement in a horizontal plane about a central axis, each reagent container holder comprising a lever and configured to hold a reagent container at an adjustable tilt with respect to the horizontal plane; a drive unit configured to adjust the tilt of one of the reagent container holders by moving a position of the lever; and a code scanner configured to read a code attached to the reagent container held by the reagent container holder to identify the reagent container, the method comprising:
determining an appropriate tilt for each of the plurality of reagent container holders based on a result of reading by the code scanner of the respective code of one or more reagent containers on the carousel,
identifying, by the controller, one or more reagent containers, on the carousel, for which corresponding one or more reagent container holders have an inappropriate tilt based on the determined respective appropriate tilt and a detected tilt of the one or more reagent container holders;
adjusting, by the drive unit, a tilt of one of the one or more reagent containers by moving the lever between a first position and a second position;
aspirating a reagent in the one of the one or more reagent containers held by the respective reagent container holder; and
detecting a signal of analyte from a measurement specimen containing a sample and the reagent aspirated.

11. The method according to claim 10, wherein
the lever is capable of being positioned at least at a first position and a second position,
the reagent container held by the reagent container holder stands at a first tilt in a state where the lever is positioned at the first position, and
the reagent container held by the reagent container holder stands at a second tilt, which is greater than the first tilt, in a state where the lever is positioned at the second position.

12. The method according to claim 10, wherein the lever is slidably arranged on a guide configured to guide a movement of the lever between the first position and the second position.

13. The method according to claim 10, wherein the lever is configured to be locked at the first position and locked at the second position.

14. The method according to claim 10, wherein the lever comprises a mark arranged to be exposed when the lever is in the first position and be retracted not to be exposed when the lever is in the second position.

15. The method according to claim 10,
wherein the sample analyzer further comprises a tilt detector configured to detect the tilt of the reagent container holder,
wherein the controller identifies one or more reagent containers, on the carousel, with an inappropriate tilt on the basis of the identification of the reagent container and a result of a detection of tilt by the tilt detector.

16. The method according to claim 15, wherein the controller refers to a configurable database defining an appropriate tilt for each of reagent IDs stored in a memory, for identifying the one or more reagent containers with an inappropriate tilt.

17. The method according to claim 15, wherein the controller generates an alert in response to identifying one or more reagent containers with an inappropriate tilt.

18. The method according to claim 15, wherein the controller outputs a screen, on a display, illustrating an arrangement of the reagent containers on the carousel, in which the identified reagent container is shown distinctively.

* * * * *